(12) United States Patent
Bernier et al.

(10) Patent No.: US 11,395,621 B2
(45) Date of Patent: Jul. 26, 2022

(54) METHOD FOR GENERATING COGNITIVE DECLINE DETECTION TOOL, METHOD FOR MEASURING COGNITIVE DECLINE AND TOOL FOR MEASURING SAME

(71) Applicant: TOUBIB MEDIA INC., Québec (CA)

(72) Inventors: Patrick Bernier, Québec (CA); Christian Gourdeau, St-Marc-des-Carrières (CA)

(73) Assignee: TOUBIB MEDIA INC., Québec (CA)

( * ) Notice: Subject to any disclaimer, the term of this patent is extended or adjusted under 35 U.S.C. 154(b) by 0 days.

(21) Appl. No.: 16/339,444

(22) PCT Filed: Oct. 4, 2017

(86) PCT No.: PCT/CA2017/051186
§ 371 (c)(1),
(2) Date: Apr. 4, 2019

(87) PCT Pub. No.: WO2018/064769
PCT Pub. Date: Apr. 12, 2018

(65) Prior Publication Data
US 2019/0231247 A1 Aug. 1, 2019

Related U.S. Application Data

(60) Provisional application No. 62/403,984, filed on Oct. 4, 2016.

(51) Int. Cl.
*A61B 5/00* (2006.01)
*G16H 50/50* (2018.01)
*G16H 50/20* (2018.01)

(52) U.S. Cl.
CPC .......... *A61B 5/4088* (2013.01); *A61B 5/7275* (2013.01); *A61B 5/742* (2013.01); *G16H 50/20* (2018.01); *G16H 50/50* (2018.01)

(58) Field of Classification Search
CPC ...... G16H 50/20; G16H 50/50; A61B 5/4088; A61B 5/7275
See application file for complete search history.

(56) References Cited

U.S. PATENT DOCUMENTS

| 5,974,124 A * | 10/1999 | Schlueter, Jr. ......... G16H 40/67 379/106.02 |
| 2013/0224117 A1 * | 8/2013 | Royall ............... G01N 33/5088 424/9.2 |

OTHER PUBLICATIONS

Dufouil et al. "Population norms for the MMSE in the very old: Estimates based on longitudinal data." Dec. 12, 2000. Neurology; 55 (11). pp. 1609-1613. (Year: 2000).*

(Continued)

*Primary Examiner* — Christopher L Gilligan
*Assistant Examiner* — Chance L Smith
(74) *Attorney, Agent, or Firm* — Carlson, Gaskey & Olds, P.C.

(57) ABSTRACT

The present invention provides a ready-to-use Cognitive Chart (CC) for follow-up of age-related cognitive decline. Similar to "growth curves", this innovative model factors in age and education to determine whether elderly patients show abnormal performance on serial MMSE and longitudinal performance tracking and favors prompt initiation of investigation and treatment. A method for generation of said charts, and a use thereof is also provided.

17 Claims, 15 Drawing Sheets

(56) References Cited

OTHER PUBLICATIONS

Bravo, G. and Hébert, R. "Age- and education-specific reference values for the Mini-Mental and Modified Mini-Mental State Examinations derived from a non-demented elderly population." Dec. 4, 1998. Int. J. Geriat. Psychiatry, 12: 1008-1018. (Year: 1998).*

Cullen, B., et al. "Screening for dementia in an Irish community sample using MMSE: a comparison of norm-adjusted versus fixed cut-points." Mar. 29, 2005. Int. J. Geriat. Psychiatry, 20: 371-376. (Year: 2005).*

Bernier, Patrick et al. "Applying 'growth curves' to age-associated cognitive decline: An innovative method to help determine normal versus abnormal longitudinal cognitive changes in the elderly." Jul. 2015. Alzheimer's & Dementia. 11. p. 711-p. 712. (Year: 2015).*

Tombaugh, T. N., et al. "Mini-Mental State Examination (MMSE) and the Modified MMSE (3MS): A psychometric comparison and normative data." 1996. Psychological Assessment, 8(1), 48-59. (Year: 1996).*

Jessen et al. "Prediction of Dementia in Primary Care Patients." Feb. 2011. PLoS One, vol. 6, Iss. 2, 1-10. (Year: 2011).*

Zhao et al. "Cognitive Decline in Patients with Alzheimer's Disease and Its Related Factors in a Memory Clinic Setting, Shanghai, China." Apr. 2014. PLoS One, vol. 9, Iss. 4, 1-8. (Year: 2014).*

Wilson, R.S., Hebert, L.E., Scherr, P.A., Barnes, L.L., Mendes De Leon, C.F., and Evans, D.A. (2009). Educational attainment and cognitive decline in old age. Neurology. 72(5). Feb. 3, 2009. pp. 460-465.

Jacqmin-Gadda, H., Fabrigoule, C., Commenges, D., and Dartigues, J-F. (1997). A 5-year longitudinal study of the mini-mental sate examination in normal aging. American Journal of Epidemiology. 145(6). 1997. pp. 498-506.

Folstein, M.F., Folstein, S.E., and McHugh, P.R. (1975). "Mini-mental state". A practical method for grading the cognitive state of patients for the clinician. Journal of Psychiatric Research. 12(3). Nov. 1975. pp. 189-198.

Stern, R.G., Mohs, R.C., Davidson, M., Schmeidler, J., Silverman, J., Kramer-Ginsberg, E., Spearcey, T., et al. (1994). A longitudinal study of Alzheimer's disease: measurement, rate, and predictors of cognitive deterioration. American Journal of Psychiatry. 151(3). Mar. 1994. pp. 390-396.

International Search Report and Written Opinion for International Application No. PCT/CA2017/051186 completed Jan. 23, 2018.

* cited by examiner

METHOD FOR GENERATING COGNITIVE DECLINE DETECTION TOOL, METHOD FOR MEASURING COGNITIVE DECLINE AND TOOL FOR MEASURING SAME

CROSS REFERENCE TO RELATED APPLICATION

This application claims the benefit under 35 U.S.C. § 119(e) of U.S. provisional patent application No. 62/403,984 which was filed on Oct. 4, 2016. The entirety of the aforementioned application is herein incorporated by reference.

FIELD OF THE INVENTION

The present invention relates to cognitive decline detection. More particularly, it relates to a ready-to-use tool named "Cognitive Chart" (CC) for the physicians to follow-up on time-dependent cognitive decline and to a method for generating such cognitive decline detection tool. As well, the present invention provides a method to model factors (such as age and education) to determine whether patients show abnormal performance on serial cognitive tests, and allows longitudinal performance tracking.

BACKGROUND

Worldwide epidemiological evidence indicates that dementia poses a serious threat to public health. Advancing age is the leading factor driving upcoming pandemic as 70% of all cases occur in people who are at least 75 years old. To this date, no curative treatment is available for Alzheimer's disease (AD), the most common cause of dementia. However, new disease-modifying therapies are tested in clinical trials and modifiable risk and protective factors can be addressed to delay AD and dementia onset before irreversible brain damage. In all cases, identifying the disease at its earliest time point before pathological brain damage is too severe, and irreversible changes in cognition and functional abilities are seen, is a major medical issue.

As a result of preventative efforts, the aging population is encouraged to seek help at the earliest cognitive change, since degenerative diseases typically have a long and progressive prodromal phase. In daily practice, however, one wonders how front-line physicians (most often Family physicians) are equipped to face the complex task of early detection? Standard dementia work-up includes basic laboratory tests, brain imaging, and cognitive screening using the Mini-Mental State Examination (MMSE) to rule out reversible conditions. When in doubt, the MMSE is repeated upon follow-up visits. Depending on the performance and whether functional decline is present, physicians will either make a diagnosis or refer the patient to a specialized memory clinic. How physicians should determine whether follow-up MMSE are compatible with age-associated cognitive decline or instead represents mild cognitive impairment or dementia remains unclear. Is a 26/30 score on the MMSE the 'normal' performance expected from a 65 year-old engineer? Or an 80 year-old retired secretary? Are we on a trajectory associated with normal aging, mild cognitive impairment (MCI) or dementia? Should the physician refer the patient to a memory clinic now or reassess in a year? Cut-off scores are quite imperfect notably for elderly individuals with limited education or if not adjusted for age and education, and they do not allow within-subject comparisons. Normative data for the Mini-Mental State Examination exist but physicians seldom use them. The fact that percentile charts do not allow easy longitudinal tracking of the cognitive trajectory may also contribute to this gap in practice.

BRIEF SUMMARY OF THE INVENTION

In a first aspect of the invention, there is provided a method for generating a tool for detecting and/or classifying cognitive decline in a patient, the method comprising: identifying at least one patient parameter variable over time in a sample of data including cognition test scores substantially influenced by the at least one patient parameter; performing a regression analysis from the sample of data and generating an original regression model therefrom; estimating parameters of the original regression model using one of a Maximum Likelihood method and a Least Mean Squares method; generating a simplified regression model from the original regression model and the estimated parameters; and generating a cognitive chart based on the simplified regression model and built using the sample of data, the cognitive chart allowing a mapping of a score at least partially based on a patient cognition test score, as a function of a second parameter at least partially based on one of the at least one patient parameter, the cognitive chart comprising a plurality of spaced apart percentile lines and a cut-off zone indicative of potential cognitive problems for the patient.

In an embodiment, the at least one patient parameter comprises an age of the patient and a number of years of schooling of the patient.

In an embodiment, the original regression model comprises at least one of the at least one patient parameter as a quadratic factor In an embodiment, the original regression model comprises the age of the patient as a quadratic factor, the number of years of schooling of the patient as a linear factor and an interaction between the age of the patient and the number of years of schooling of the patient, the original regression model being defined as:

$$M = \beta_0 + \beta_1 A + \beta_2 A^2 + \beta_3 E + \beta_4 A \cdot E$$

wherein M corresponds to the patient cognition test score, A corresponds to the age of the patient, E corresponds to the number of years of schooling of the patient and $\beta_0$, $\beta_1$, $\beta_2$, $\beta_3$, $\beta_4$ each correspond to a constant.

In an embodiment, the simplified regression model is defined as:

$$\frac{M}{A} = \beta_1 + \beta_2\left(A + \frac{\beta_4}{\beta_2}E\right).$$

In an embodiment, the step of generating the cognitive chart based on the simplified regression model further comprises defining at least one standardized parameter from the simplified regression model and using each one of the at least one standardized parameter as an axis of the cognitive chart.

In an embodiment, the at least one standardized parameter comprises a cognitive quotient (QuoCo) defined as:

$$QuoCo = (M/A) \cdot C_1$$

wherein M corresponds to the patient cognition test score, A corresponds to the age of the patient and $C_1$ corresponds to a first constant.

In an embodiment, the at least one standardized parameter comprises a standardized age ($S_A$) defined as:

$$A-(C_2*E)$$

wherein A corresponds to the age of the patient, $C_2$ corresponds to a second constant and E corresponds to the number of years of schooling of the patient.

In an embodiment, the at least one standardized parameter is configured to define a linear simplified regression model used for generating the cognitive chart.

In an embodiment, the method further comprises the step of displaying the cognitive chart on a digital medium or a physical medium, for subsequent use in aiding detection, diagnosis or follow-up of cognitive decline in a patient.

In an embodiment, the step of displaying the cognitive chart on the digital medium or the physical medium comprises printing the cognitive chart on the physical medium.

In accordance with another general aspect, there is provided a computer readable memory having recorded thereon statements and instructions for execution by a computer, with the statements and instructions comprising code for performing the steps of the method for generating a tool for detecting and/or classifying cognitive decline in a patient.

In accordance with another general aspect, there is provided a computer program product comprising a computer readable memory storing computer executable instructions thereon that when executed by a computer, perform the steps of the method for generating a tool for detecting and/or classifying cognitive decline in a patient.

In accordance with a further aspect, the invention provides a method for diagnosing or classifying cognitive decline in a patient, the method comprising the steps of: determining a cognitive test score for said patient; noting age of said patient; noting number of years of schooling of said patient; calculating a cognitive quotient (QuoCo) as QuoCo=test score/age×constant1 for said patient; calculating a patient parameter variable; plotting at least a first QuoCo measure point and, optionally, an additional QuoCo measure point, on a cognitive chart (CC) for the corresponding patient parameter variable, said CC being as defined in FIG. 3, 7 or 8.

In an embodiment, the cognitive chart is defined as CHART 2 shown in FIG. 3 and the step of calculating a patient parameter variable includes calculating a standardized age $(S_A)$ as: $S_A$=age−constant$_2$×# years of schooling for said patient. The cognitive decline status of the patient is carried out by determining at least one of: whether any single contemporaneous QuoCo point is positioned within a grey cut-off zone of CHART 2 as defined in FIG. 3, whereby the patient is then classified as having potential cognitive problems; or whether a single contemporaneous QuoCo point is positioned within a white zone of said chart, whereby the patient is then classified as potentially having no cognitive problem; or drawing a line connecting the first QuoCo measure point to the additional QuoCo measure point; whereby when said line shows a decline greater than an allotted width of a percentile zone from said first QuoCo measure point (e.g. started on the 85th and crossed the 65th from CHART 2), the patient is then classified as having potential cognitive problems.

In an embodiment, the cognitive quotient is defined as QuoCo=test score/age×1000.

In an embodiment, the standardized age $(S_A)$ is defined as: age−0.5×# years of schooling for said patient.

In an embodiment, the cognitive test includes a Mini-Mental State Examination (MMSE).

In accordance with another general aspect, there is provided a computer readable memory having recorded thereon statements and instructions for execution by a computer, with the statements and instructions comprising code for performing the steps of the method for diagnosing or classifying cognitive decline in a patient.

In accordance with another general aspect, there is provided a computer program product comprising a computer readable memory storing computer executable instructions thereon that when executed by a computer, perform the steps of the method for diagnosing or classifying cognitive decline in a patient.

In accordance with another general aspect, there is provided a tool for aiding diagnosis of cognitive decline in a patient at risk thereof, said tool comprising a cognitive CHART 2 as defined in FIG. 3; wherein QuoCo is a MMSE score divided by age of said patient×1,000, and $S_A$ is an age of said patient minus 0.5×# years of schooling.

According to a further aspect, there is provided a CHART 2 for determining status of cognitive decline in a patient, said CHART 2 being as defined in FIG. 3.

According to a further aspect, there is provided a use of CHART 2 for determining status of cognitive decline in a patient, said CHART 2 being as defined in FIG. 3.

According to a further aspect, there is provided a use CHART 2 as defined above, wherein said determining is carried out by assessing whether any single contemporaneous QuoCo point is positioned within a grey cut-off zone of said CHART 2, whereby the patient is then classified as having potential cognitive problems.

According to a further aspect, there is provided a use CHART 2 as defined above, wherein said determining is carried out by assessing whether a single contemporaneous QuoCo point is positioned within a white zone of said CHART 2, whereby the patient is then classified as likely to have no cognitive problem.

According to a further aspect, there is provided a use of CHART 2 as defined above, wherein said determining is carried out by drawing a line connecting a first QuoCo measure point to a second QuoCo measure point; whereby when said line shows a decline greater than an allotted width of a percentile zone from said first QuoCo measure point in CHART 2, the patient is then classified as having potential cognitive problems.

According to a further aspect, the invention provides a kit for helping physicians to diagnose or classify cognitive decline in a patient, said kit comprising: the cognitive CHART 2 as defined in FIG. 3; instructions on how to calculate QuoCo and $S_A$; instructions on how to plot QuoCo on said CHART 2 as a function of said $S_A$; and instructions on how to interpret plot on said CHART 2 for aiding diagnosis or classification of cognitive decline of said patient.

In an embodiment, the kit further comprises a MMSE questionnaire.

In an embodiment, the kit consists essentially of a computer program executable on an electronic device.

BRIEF DESCRIPTION OF THE FIGURES

Other objects, advantages and features will become more apparent upon reading the following non-restrictive description of embodiments thereof, given for the purpose of exemplification only, with reference to the accompanying drawings in which:

FIG. 5A represents a case of dementia as shown by QuoCo, whereas the MMSE data alone could have been interpreted as normal; FIG. 5B represents a case of normal QuoCo trajectory, whereas the MMSE data alone would have been interpreted as suspect; and FIG. 5C represents cases of 3 different patients, each with good MMSE scores and high schooling (15 years), but with a 10 years age difference; and shows that the younger patient has potential cognitive decline, whereas the older ones don't.

DETAILED DESCRIPTION

Abbreviations

Figure 1B:
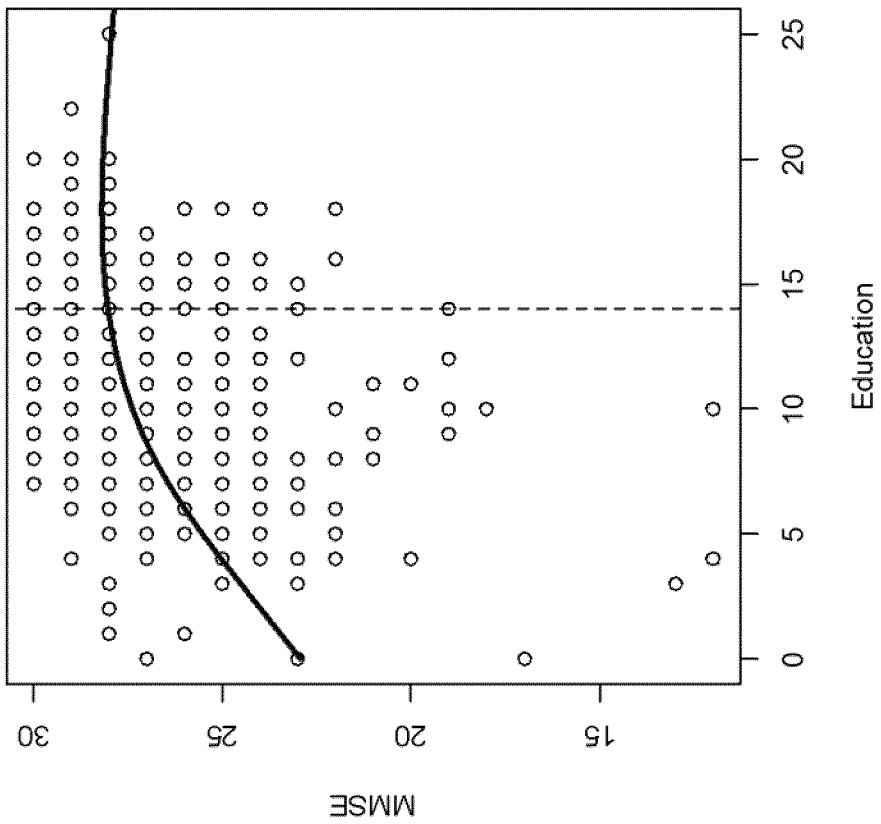
FIGS. 1*a* and 1*b* are graphical representations showing respectively a relationship between age and MMSE test (FIG. 1*a*), and education and MMSE test (FIG. 1*b*).

In the present description, the following abbreviations can be used in order to simplify the text and ease the lecture thereof: AD: Alzheimer's Disease; CC: Cognitive Chart; CIND: Cognitive Impairment No Dementia; CSHA: Canadian Study of Health and Aging; HC: Healthy Controls; MoCA: Montreal Cognitive Assessment test; MCI: Mild Cognitive Impairment; MMSE: Mini-Mental State Examination; NACC's UDS: National Alzheimer's Coordinating Center's Uniform Data Set; QuoCo: Cognitive Quotient; $S_A$: Standardized Age; GPCOG: General Practitioner Assessment of Cognition; MIS: Memory impairment screen; ADAS-cog: Alzheimer's Disease Assessment Scale-Cognitive Subscale.

Definitions

The term "about" as used herein refers to a margin of + or −10% of the number indicated. For sake of precision, the term "about" when used in conjunction with, for example: 90% means 90%+/−9% i.e. from 81% to 99%. More precisely, the term "about" refers to + or −5% of the number indicated, where for example: 90% means 90%+/−4.5% i.e. from 86.5% to 94.5%.

As used herein the singular form "a" means "at least one" and therefore includes plural referents unless the context clearly dictates otherwise. Thus, for example, reference to "a patient" includes a plurality of such patients and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used in this specification and claim(s), the expression "electronic device" means any device for storing and processing data, typically in binary form, according to instructions. For example and without being limitative, the expression "electronic device" can include, but is not limited to, smartphones, electronic tablets, personal digital assistants, desktop computers, laptop computers, servers and other wireless communication devices or combinations thereof. The electronic device can include elements such as, without being limitative, a display device, an input device(s), a memory, at least one processor, and any other component required for proper functioning thereof.

Description of Embodiments

Herein presented is a ready-to-use tool configured to measure cognitive abilities and follow-up of cognitive decline and a method for generating such tool. The tool can be referred to as a Cognitive Chart (CC). This Cognitive Chart allows simple clinical follow-up of age-related cognitive decline by first-line physicians using cognitive tests such as for example, the MMSE test, or the MoCA test, or any other test that can measure cognitive decline. For example and without being limitative, other cognitive tests that can be used includes the GPCOG test, the ADAS-cog test, the Mini-Cog™ test, the MIS test or the like.

Method of Generating Chart

Therefore, in accordance with a first embodiment of a first aspect, there is provided a method for generating a tool for detecting cognitive decline in a patient. The method includes an initial step of identifying at least one patient parameter variable over time in a sample of data including cognition test scores substantially influenced by the at least one patient parameter. For example and without being limitative, in an embodiment, the at least one patient parameter can include an age of the patient and a number of years of schooling of the patient. One skilled in the art will however understand that, in an alternative embodiment, other parameters such as, for example and without being limitative gender, profession, medical condition, ethnic origin, intellectual capacity or the like can also be used. In an embodiment and as will be described in more details below, the sample of data including cognition test scores substantially influenced by the at least one patient parameter includes a training sample from the CSHA and a validation sample from the NACC's UDS. One skilled in the art will understand that, in an alternative embodiment, only one of the above-mentioned samples can be used. Moreover, in another alternative embodiment, other samples offering a sufficient representability and quality of data can also be used.

The method further includes the steps of performing a regression analysis from the sample of data and generating an original regression model therefrom. In an embodiment, at least one parameter of the original regression model is a quadratic factor. More particularly, in an embodiment the original regression model may comprise the age of the patient as a quadratic factor, the number of years of schooling of the patient as a linear factor and an interaction between the age of the patient and the number of years of schooling of the patient. In such an embodiment, the original regression model is defined as:

$$M = \beta_0 + \beta_1 A + \beta_2 A^2 + \beta_3 E + \beta_4 A \cdot E$$

wherein M corresponds to the patient cognition test score, A corresponds to the age of the patient, E corresponds to the number of years of schooling of the patient and $\beta_0$, $\beta_1$, $\beta_2$, $\beta_3$, $\beta_4$ each correspond to a constant.

The method further includes the steps of: estimating parameters of the original regression model using one of a Maximum Likelihood method and a Least Mean Squares method; and generating a simplified regression model from the original regression model and the estimated parameters. According to a particular embodiment, the simplified regression model is defined as:

$$\frac{M}{A} = \beta_1 + \beta_2 \left( A + \frac{\beta_4}{\beta_2} E \right).$$

wherein, once again, M corresponds to the patient cognition test score, A corresponds to the age of the patient, E corresponds to the number of years of schooling of the patient and $\beta_1$, $\beta_2$ and $\beta_4$ each correspond to a constant. As will be easily understood by one skilled in the art, in an embodiment, the above-mentioned simplified regression model can be obtained from a deduction that $\beta_0$ and $\beta_3$ from the original regression model are not significantly different from 0, using parameter estimation based on results which will be presented in the examples below.

Figure 7:
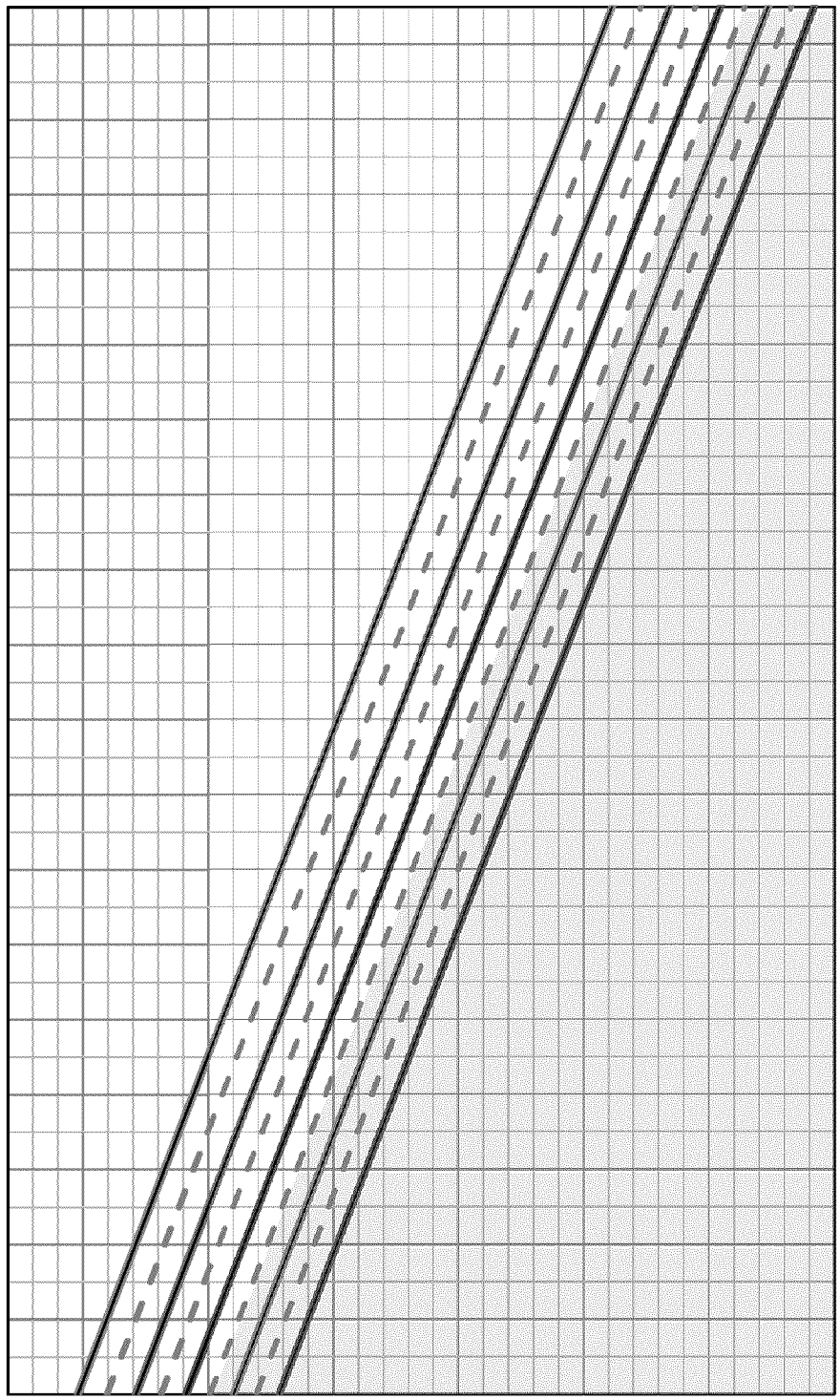
FIG. 7 shows a generic Cognitive Chart where each solid parallel line represents a generic percentile found by a generic cognitive decline test, such as for example and without being limitative a MoCA test.

Finally, the method includes the step of generating a cognitive chart based on the simplified regression model and built using the sample of data. The cognitive chart allows a mapping of a score at least partially based on a patient's cognition test score (i.e. a score that either depends entirely from a score obtained by the patient in a cognition test or is a derivative thereof), as a function of a second parameter at least partially based on one of the at least one patient parameter (i.e. a parameter that either depends entirely from the at least one patient parameter or is a derivative thereof). In an embodiment, the generated cognitive chart includes a plurality of spaced apart percentile lines which allow detection of abnormal cognitive decline over time, as will be described in more details below. In the embodiment shown, the generated cognitive chart also includes, a cut-off zone indicative of potential cognitive problems for the patient. In the embodiment shown, the cut-off zone indicative of potential cognitive problems for the patient is a grey area, positioned in the portion of the cognitive chart where the mapping of a patient result is in indication of potential cognitive problems. The Cognitive CHART 1 and the Cognitive CHART 2, shown below in the description (and reproduced in FIG. 7 and FIG. 3), are exemplary embodiments of the Cognitive chart generated based on the simplified regression model and built using the sample of data.

In accordance with a particular embodiment, the step of generating the cognitive chart based on the simplified regression model further comprises defining at least one standardized parameter from the simplified regression model and using each one of the at least one standardized parameter as an axis of the cognitive chart. In the embodiment shown, the at least one standardized parameter comprises a cognitive quotient (QuoCo) which can be defined as:

$$QuoCo = (M/A) * C_1$$

wherein M corresponds to the patient cognition test score, A corresponds to the age of the patient and $C_1$ corresponds to a first constant.

In the embodiment shown, the at least one standardized parameter further comprises a standardized age ($S_A$) defined as:

$$A - (C_2 * E)$$

wherein A corresponds to the age of the patient, $C_2$ corresponds to a second constant and E corresponds to the number of years of schooling of the patient.

As will be better understood in view of the description of the examples below, in the embodiment shown, the standardized parameters (Cognitive quotient (QuoCo) and the standardized age ($S_A$)) are configured to define a linear simplified regression model used for generating the cognitive chart.

According to a particular embodiment, the method as defined hereinabove further comprises a step of displaying the generated cognitive chart on a digital medium (such as for example a display of an electronic device or any other digital display) or a physical medium (such as a sheet pf paper, a cardboard, a poster, etc.), for subsequent use in aiding detection, diagnosis or follow-up of cognitive decline in a patient by a clinician. One skilled in the art will understand that, in an embodiment, the step of displaying the cognitive chart on the digital medium or the physical medium can include a step of printing the cognitive chart on the physical medium (i.e. on the sheet of paper, cardboard, poster, etc.).

One skilled in the art will understand that, according to a particular embodiment, the method can be a computer implemented method. Hence, in an embodiment, the above described steps of: identifying at least one patient parameter variable over time in a sample of data including cognition test scores substantially influenced by the at least one patient parameter; performing a regression analysis from the sample of data and generating an original regression model therefrom; estimating parameters of the original regression model using one of a Maximum Likelihood method and a Least Mean Squares method; generating a simplified regression model from the original regression model and the estimated parameters; and generating a cognitive chart based on the simplified regression model and built using the sample of data can be computer steps performed by an electronic device having instructions stored in a memory for performing the steps. In an embodiment, the computer implemented method can include a further step of storing the generated cognitive chart (or the data relative thereto) in a memory of an electronic device.

In an embodiment, a computer implemented method can also comprise the steps of receiving patient parameter(s) through the input device(s) of the electronic device (i.e. any possible component for inputting data to the electronic device) and computing the data, by the processor of the electronic device of the patient parameter(s), based on the cognitive chart, to determine whether the patient should be classified as having potential cognitive problems. The method can also include the further step of outputting a result indicative of whether the patient should be classified as having potential cognitive problems. For example and without being limitative, the step of outputting a result indicative of whether the patient should be classified as having potential cognitive problems can be performed through the display of the result on the display of the electronic device.

In view of the above, it will be understood that, in an embodiment, there can be provided a computer readable memory having recorded thereon statements and instructions for execution by a computer, with the statements and instructions comprising code for performing the above-describe steps of the described computer implemented method. In another embodiment, there can also be provided a computer program product comprising a computer readable memory storing computer executable instructions thereon that when executed by a computer, perform the method steps of the above described computer implemented method.

Method of Diagnosis of Cognitive Decline

According to an embodiment, there is also provided a method for diagnosing or classifying cognitive decline in a patient based on a cognitive chart for which the method for generation thereof has been described above.

The method includes the initial steps of: determining a cognitive test score for said patient; noting (or obtaining) the age of said patient; noting (or obtaining) the number of years of schooling of said patient (# year of schooling). In an embodiment, the cognitive test score is obtained from the Mini-Mental State Examination (MMSE) well known to those in the art. As mentioned above, one skilled in the art will however understand that, in an alternative embodiment, the cognitive test score can be determined based on a cognition test different for the MMSE test, such as, for example and without being limitative, the MoCA test.

In an embodiment, based on the cognitive test score, patient's age and patient's years of schooling, the method for diagnosing or classifying cognitive decline in a patient further includes calculating a cognitive quotient (QuoCo) and a standardized age ($S_A$) for the patient. In an embodiment, the QuoCo can be defined as "QuoCo=test score/age× constant1" for the patient. The standardized age can be defined as: "$S_A$=age−constant2×# years of schooling" for said patient. More particularly, in an embodiment, the cognitive quotient can be calculated using constant1=1000 and constant2±0.5, such that: "QuoCo=test score/age×1000" and the standardized age ($S_A$) is: "age−0.5×# years of schooling" for the patient.

In an embodiment, the method for diagnosing or classifying cognitive decline in a patient based on the cognitive chart, further includes plotting at least a first QuoCo measure point on a cognitive chart (CC), for a corresponding patient parameter variable. In an embodiment, the cognitive chart (CC) is defined as the cognitive chart of CHART 1.

Based on the plotting of the at least first QuoCo point on the cognitive chart (CC) CHART 1 shown above, the method for diagnosing or classifying cognitive decline in a patient based on a cognitive chart can include classifying the patient as having potential cognitive problems when the first QuoCo measure point (i.e. a single contemporaneous QuoCo point) is positioned within a grey cut-off zone of CHART 1 (i.e. is positioned within the cut-off zone indicative of potential cognitive problems) or classifying the patient as likely to have no cognitive problem when the first QuoCo measure point (i.e. a single contemporaneous QuoCo point) is positioned within a white zone of said chart (i.e. is positioned outside of the cut-off zone indicative of potential cognitive problems).

In an embodiment, a plurality of QuoCo points can be plotted on the cognitive chart (CC). The plurality of QuoCo points can each represent a value of the QuoCo of the patient associated to different value of the patient parameter variable. For example and without being limitative, in an embodiment where the patient parameter variable is a Standardized age ($S_A$) of the patient, the plurality of QuoCo points can each represent a value of the QuoCo of the patient associated to different $S_A$ of the patient taken over time. When a plurality of QuoCo points are plotted on the cognitive chart (CC), the method for diagnosing or classifying cognitive decline in a patient based on a cognitive chart can include drawing a line connecting a first QuoCo measure point and a second QuoCo measure point. If said line shows a decline greater than an allotted width of a percentile zone between the first QuoCo measure point and the second QuoCo measure point in CHART 1, the method includes classifying the patient as having potential cognitive problems.

According to a particular embodiment of the present method, CHART 1 is particularly defined as CHART 2.

In view of the above, in an embodiment where the cognitive chart corresponds to the cognitive chart of CHART 2 (See FIG. 3), the method for diagnosing or classifying cognitive decline in a patient can include the steps of: determining a cognitive test score for said patient; noting (or obtaining) the age of said patient; noting (or obtaining) the number of years of schooling of said patient (# year of schooling); calculating a cognitive quotient (QuoCo) corresponding to: "QuoCo=test score/age×1000" for said patient; calculating a standardized age ($S_A$) corresponding to: "$S_A$=age−0.5×# years of schooling" for said patient; plotting at least a first QuoCo point and, optionally, an additional QuoCo point, on a cognitive chart (CC) for a corresponding Standardised age ($S_A$), said CC being defined as CHART 2 (see CHART 2 above and FIG. 3); and determining at least one of:

whether any single contemporaneous QuoCo point is positioned within a grey cut-off zone of said CHART 2, to classify the patient as having potential cognitive problems;

whether a single contemporaneous QuoCo point is positioned within a white zone of said CHART 2, to classify the patient as likely to have no cognitive problem; or drawing a line connecting the first QuoCo measure point to the additional QuoCo measure point, to classify the patient as having potential cognitive problems if said line shows a decline greater than an allotted width of a percentile zone between the first QuoCo measure point and the additional QuoCo measure point in CHART 2.

Figure 3:
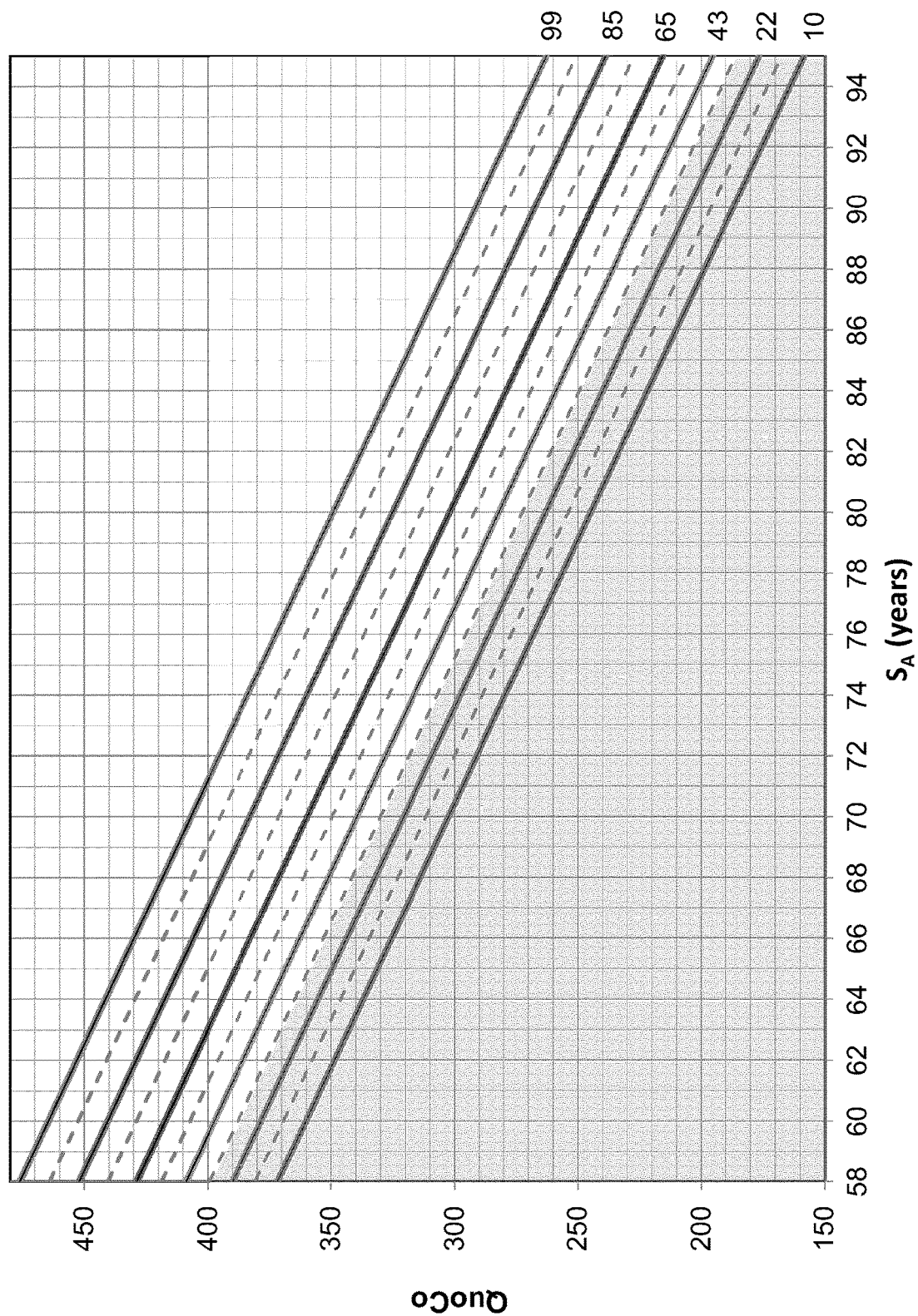
FIG. 3 is a Cognitive Chart where each solid parallel line represents a percentile. The percentile lines representing respectively (from top to bottom) the 99th percentile, the 85th percentile, the 65th percentile, the 43rd percentile, the 22nd percentile, and the 10th percentile.
Figure 8:
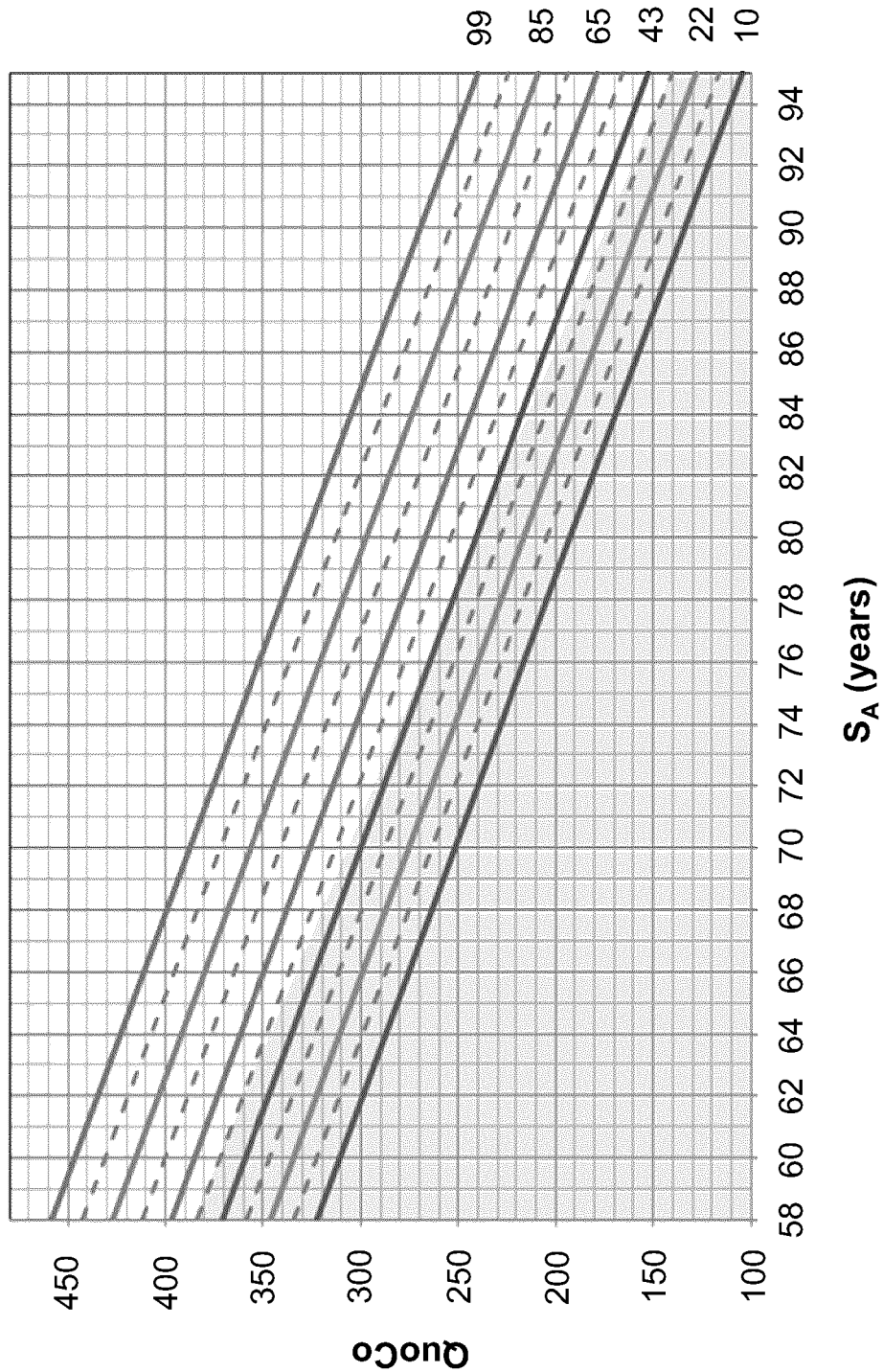
FIG. 8 shows a hypothetical Cognitive Chart where each solid parallel line represents a hypothetical percentile found by the MoCA test.

One skilled in the art will understand that, in an alternative embodiment, the method for diagnosing or classifying cognitive decline in a patient can be performed using cognitive charts (CC) defined by charts different form the above-mentioned CHART 1 (FIG. 7) and CHART 2 (FIG. 3). For example, in an embodiment where the cognitive test score is obtained from another test such as, for example, the MoCA test, a specific chart for this test can be used. For example and without being limitative, FIG. 8 shows a hypothetical Cognitive Chart where each solid parallel line represents a hypothetical percentile found by the MoCA test.

One skilled in the art will understand that, according to a particular embodiment, the method for diagnosing or classifying cognitive decline in a patient can be a computer implemented method. Hence, in an embodiment, the above described steps can be computer steps performed by an electronic device having instructions stored in a memory for performing the steps. Moreover, it will be understood that, in an embodiment, there can be provided a computer readable memory having recorded thereon statements and instructions for execution by a computer, with the statements and instructions comprising code for performing the above-describe steps of the described method for diagnosing or classifying cognitive decline in a patient. In another embodiment, there can also be provided a computer program product comprising a computer readable memory storing computer executable instructions thereon that when executed by a computer, perform the method steps of the above described method for diagnosing or classifying cognitive decline in a patient.

Tool for Diagnosis of Cognitive Decline

According to a particular aspect, the present invention also provides a tool for aiding diagnosis of cognitive decline in a patient at risk thereof. The tool includes a cognitive chart defined as CHART 2 as defined above, wherein, as described above the QuoCo is a MMSE score divided by age of said patient×1,000 (QuoCo=test score/age×1000), and $S_A$ is an age of said patient minus 0.5 multiplied by the number of years of schooling of the patient ($S_A$=age−0.5×# years of schooling).

Use of Cognitive Chart (CC)

According to a further aspect, the invention also provides a chart for use in determining a status of cognitive decline in a patient. In an embodiment, the chart is defined as the chart shown in CHART 2, as defined above. In CHART 2, the vertical axis represents a value of the QuoCo, which can be defined as a MMSE score divided by the age of said patient×1,000 (QuoCo=test score/age×1000) and the horizontal axis represents a value of a standardized age, which can be defined as an age of said patient minus 0.5 multiplied by the number of years of schooling of the patient ($S_A$=age−0.5×# years of schooling). One skilled in the art will however understand that, in an alternative embodiment, the chart could differ from the chart shown in CHART 2.

Particularly, in accordance with the use of the cognitive chart (CC), in an embodiment, the cognitive decline status of the patient is carried out by determining whether any single contemporaneous QuoCo point is positioned within a grey cut-off zone of said chart (i.e. is positioned inside the cut-off zone indicative of potential cognitive problems). If any single contemporaneous QuoCo point is positioned within the grey cut-off zone of said chart, the patient is classified as having potential cognitive problem.

Still in accordance with the use of the cognitive chart (CC), in an embodiment, the cognitive decline status of the patient is carried out by assessing whether a single contemporaneous QuoCo point is positioned within a white zone of said chart (i.e. is positioned outside of the cut-off zone that is indicative of potential cognitive problems). If the single contemporaneous QuoCo point is positioned within a white zone of said chart, the patient is classified as likely to have no cognitive problem.

Still in accordance with the use of the cognitive chart (CC), in an embodiment, alternatively, the cognitive decline status of the patient is carried out by drawing a line connecting a first (or earlier) QuoCo measure point to an additional (or later) QuoCo measure point. If the line shows a decline greater than an allotted width of a percentile zone between the first (or earlier) QuoCo measure point and the additional (or later) QuoCo measure point in the chart (e.g. the first QuoCo measure point is positioned above the 85th percentile line and the additional QuoCo measure point is positioned below the 65th percentile line, thereby crossing a percentile line), then the patient is classified as having potential cognitive problems.

Still, in accordance with a particular embodiment, there is provided a use of CHART 2 as defined in FIG. 3, for the manufacture of a display item for helping physicians in diagnosing or determining a status of cognitive decline in a subject, more particularly a patient. Furthermore, the display item may be selected from the group consisting of: a poster, a board, a screen, a pad, a picture, a playbill, a billboard, advertisement, a placard and a notice.

Kit

According to a further aspect, there is also provided a kit for helping physicians to diagnose or classify cognitive decline in a patient. Said kit includes: the cognitive chart (CC) as defined herein; instructions on how to calculate QuoCo and $S_A$; instructions on how to plot QuoCo on said CC as a function of said $S_A$; and instructions on how to interpret the QuoCo measure points plotted on the CC, for aiding diagnosis or classification of cognitive decline of said patient.

According to a particular embodiment of the kit of the invention, the kit further comprises a MMSE or a MoCA questionnaire, and/or any other cognitive decline tests known in the art, which can be used in the calculation of a QuoCo of a patient to be mapped on a Cognitive Chart (CC).

More particularly, the kit may be included as part of a computer program product comprising a computer readable memory storing data relative to the CC and computer executable instructions thereon that when executed by a computer, perform calculation of the QuoCo and the $S_A$ and the steps of the method for diagnosing or classifying cognitive decline in a patient.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

EXAMPLES

Example 1 presents step-by-step the methods used to develop the present CC. Example 2 presents a comprehensive description of the training sample from CSHA as well as the validation sample from the National Alzheimer's Coordinating Center's (NACC) Uniform Data Set (UDS) study. Statistical modeling and the regression model are presented in Example 3. Then, in Example 4, the QuoCo and $S_A$ are introduced as key indicators of age-associated cognitive decline related to MMSE. External validation of the model using data from the NACC's UDS follows in Example 5. Finally, Example 6 shows the final validated CC.

Example 1—Model Fitting

Methods

Study Samples

The study used two samples of participants. First, a training sample from the CSHA which was used for model building. Second, a validation sample from the NACC's UDS which was used for external validation.

The training sample was composed of participants from the CSHA, a major Canadian endeavor conducted to estimate the prevalence and incidence of dementia and its subtypes by age group in five Canadian regions. A representative sample of 9,008 patients aged 65 and over was randomly selected from Medicare lists in nine provinces or from the Enumeration Composite Record in Ontario and was first interviewed in February 1991. This study was approved by institutional review boards at all 18 participating Canadian centers, grouped in five geographic regions (British Columbia, the Prairies, Ontario, Quebec and the Atlantic region). Written informed consent was obtained from all participants or their legal representatives. Of the 9,008 participants, patients who received a diagnosis of cognitive impairment no dementia (CIND) during CSHA without developing dementia (1,269 patients) were excluded (CIND were nonetheless explored in the Part II—Application of Cognitive Charts—see Example 5). Patients who had complex and abnormal diagnostic paths (170 patients) (i.e. patients who oscillated back and forth between normal and impaired cognition) were also excluded. As such, 6,411 patients who remained normal (healthy controls or HC) throughout the 10-year course of the study between 1991 and 2001 (see Table 1) were included. The 1,158 patients who developed dementia over the course of the study were also included (to estimate the performance of the model).

TABLE 1

Composition of the training sample from CSHA.

| | Healthy Controls (n = 6,411) | Dementia (n = 1,158)[a] |
|---|---|---|
| Age at study start (mean, sd) | 76.04 (6.90) | 80.79 (6.67) |
| Years of education (mean, sd) | 10.49 (3.78) | 9.35 (3.88) |
| MMSE score at study start (mean, sd) | 27.07 (2.69) | 23.71 (5.14) |
| MMSE decline at end of study (mean, sd) | −0.54 (2.64)[b] | −6.70 (5.94)[c] |

[a]1,158 patients developed dementia over the course of the study, including 361 prevalent cases of dementia.
[b]3,951 patients who remained normal through the course of the study had at least one follow-up MMSE.
[c]695 patients who developed dementia during the course of the study had at least one follow-up MMSE.
Abbreviations: CSHA: Canadian Study of Health and Aging; MMSE: Mini-Mental State Examination The external validation sample was obtained through the NACC's UDS open access data process. This is a valuable resource for the AD research community because of its sample size, power, and comparability. The NACC's UDS reflects the total enrollment at the Alzheimer's Disease Centers (ADC) since 2005 and includes patients with a range of cognitive status—normal cognition, MCI, and demented. Patients are enrolled through clinician referral, self-referral by patients or family members, active recruitment through community organizations, and volunteers who wish to contribute to research. Most Centers also enroll volunteers with normal cognition, and these tend to be highly educated. Data are collected via a standardized evaluation. Written informed consent is obtained from all participants and informants. Diagnosis is made by either a consensus team or a single physician (the one who conducted the examination). The data is longitudinal, and its protocol requires approximately annual follow-up as long as the patient is able to participate.

For validation purposes, NACC's UDS' patients who were healthy at study start and either remained healthy over the course of the study (i.e. external validation) or developed dementia (i.e. application of CC, see Example 6) was obtained. Of 6,501 patients included, 6,000 remained normal and 501 developed dementia. Table 2 presents the composition of the validation sample. Overall, participants were slightly younger, more educated and cognitively healthier at study start than the training sample. Furthermore, incidence of delirium appeared lower in the NACC's UDS sample.

TABLE 2

Composition of the validation sample from NACC's UDS.

| | Normal (n = 6,000) | Dementia (n = 501) |
|---|---|---|
| Age at study start (mean, sd) | 72.93 (7.76) | 79.87 (7.07) |
| Years of education (mean, sd) | 15.71 (3.00) | 15.00 (3.25) |
| MMSE score at study start (mean, sd) | 28.98 (1.34) | 28.24 (1.77) |
| MMSE decline at end of study (mean, sd) | −0.08 (1.45)[a] | −5.36 (5.33)[b] |

[a]5,864 patients who remained normal through the course of the study had at least one follow-up MMSE.
[b]486 patients who developed dementia during the course of the study had at least one follow-up MMSE.
Abbreviations: MMSE: Mini-Mental State Examination; NACC's UDS: National Alzheimer's Coordinating Center's Uniform Data Set[21].

Example 2—Measurement of Disability, Dementia, and Severe Cognitive Impairment in CSHA The training sample is a very well-studied sample of HC. Eligibility criteria of the CSHA are extensively described in previous publications. Diagnostic criteria for dementia followed the fourth revision of the Diagnostic and Statistical Manual of Mental Disorders, and those for AD were based on the criteria of the National Institute of Neurological and Communicative Disorders and Stroke and the Alzheimer's Disease and Related Disorders Association.

In brief, a nurse first registered the patients, completed consent forms, administered the Modified Mini-Mental State (or 3MS) exam, tested hearing, vision and vital signs, recorded height, weight and medication use, and obtained the patient's cognitive and family history from a relative, using section H of the Cambridge Mental Disorders of the Elderly Examination. Second, a psychometrician, blind to the 3MS score from the interview, administered a battery of neuropsychological tests to patients with a score of 50 or more on the 3MS exam given by the nurse (i.e. patients were excluded if their score was less than 50 on the 3MS). A neuropsychologist evaluated the test results in conjunction with the results of the CAMDEX and the 3MS. Third, a physician reviewed the information collected by the nurse and examined the patient, performing a mental status assessment as well as physical and neurologic examinations. The physician then made a preliminary diagnosis before seeing the neuropsychologist's evaluation. Finally, patients suspected of having dementia or delirium were sent for hematologic and biochemical tests. A case conference was then held to arrive at a consensus diagnosis in one of the following categories: no cognitive loss, cognitive loss but no dementia (eight subcategories were specified), AD (probable or possible, divided into four subcategories), vascular dementia (four subcategories), other specific dementia (six subcategories) or unclassifiable dementia.

The CSHA group selected the 3MS because of its coverage of relevant aspects of cognitive impairment, the quality of its documentation and its validity. The 3MS exam adds several questions to the MMSE (i.e. spelling 'WORLD' backward) to expand its scope. It uses a more sophisticated scoring system but permits the computation of MMSE scores, which was done within CSHA. Data used to model the CC presented herein is based on MMSE scores from CSHA.

Example 3—Statistical Modeling

Initial analyses of the training sample from CSHA suggested that a linear model taking into account age and education could predict MMSE scores. Considering that patients had up to three measures in the CSHA, the model was investigated using repeated measures regression analyses. Three correlation structures were explored (compound symmetry, order 1 autoregressive, and variance components) and compound symmetry, which presented the lowest AIC (Akaike Information Criterion) was chosen. Attempt to extract a theoretical working model from the data-driven results were performed. All analyses were performed using SAS 9.4.

Figure 1A:
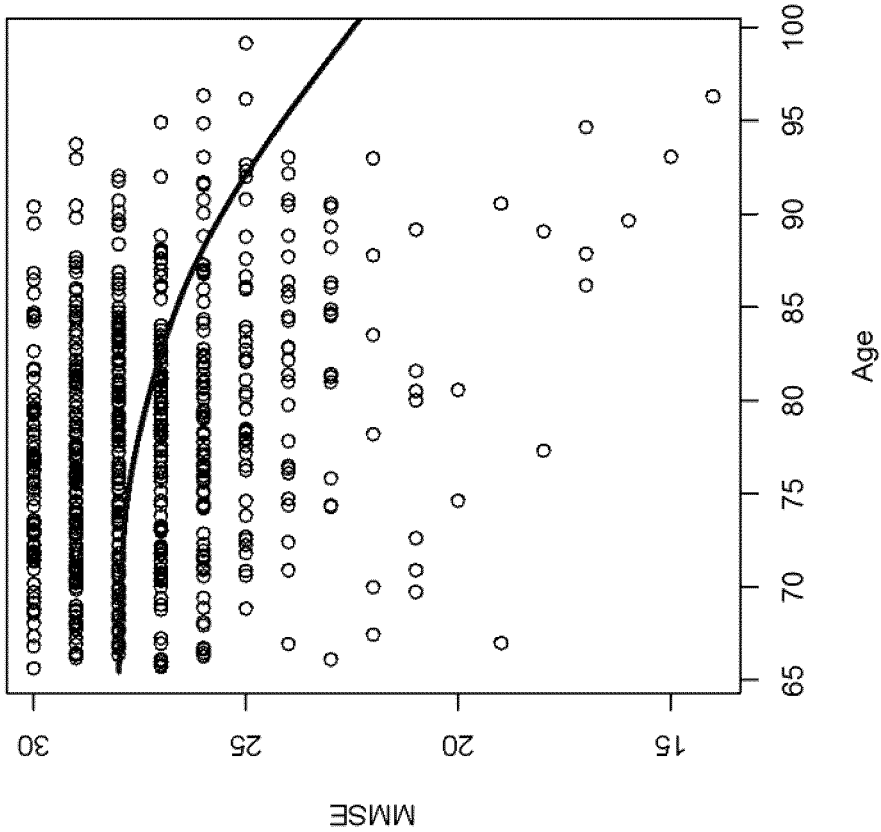

The relationship between predictors of cognitive decline and MMSE were initially explored. FIGS. 1a and 1b illustrate the relationship between: FIGS. 1a) age and MMSE, and 1b) education and MMSE. As suggested by cubic smoothing splines, it was postulated that age was quadratically associated with MMSE while a linear relationship appeared between education and MMSE; the latter becoming null past 14 years of education (interestingly, this corresponds to the difference between having non-college vs. college education). Of note, regression analyses indicated similar relationships.

Developing a Regression Model

Both observations discussed above led us to propose a candidate regression model for MMSE (M) that would include age (A) as a quadratic factor, education (E) which was recoded past the 14 years cut point as a linear factor, and an interaction between age and education.

$$\text{Model 1:} \quad M = \beta_0 + \beta_1 A + \beta_2 A^2 + \beta_3 E + \beta_4 A \cdot E$$

Because of correlated errors due to repeated measures, the parameters of the regression model were estimated using Maximum Likelihood methods for repeated measures. Using the AIC, it was found that a compound symmetry correlation structure fit the data appropriately. Table 3 presents the parameter estimates, confidence interval bounds and significance levels of Model 1.

TABLE 3

Parameter estimates and significance level.

| Parameter | Estimate | P-value | 95% lower bound | 95% upper bound |
|---|---|---|---|---|
| $\beta_0$ | −1.791 | 0.46 | −6.5 | 2.9 |
| $\beta_1$ | 0.786 | <0.001 | 0.67 | 0.90 |
| $\beta_2$ | −0.00577 | <0.001 | −0.0065 | −0.0051 |
| $\beta_3$ | 0.0547 | 0.52 | −0.11 | 0.22 |
| $\beta_4$ | 0.00297 | <0.001 | 0.00086 | 0.0051 |

Simplifying the Model for Practical Use

Applying simple algebra, Model 1 was reformulated in the following way to allow further simplifications.

$$\text{Model 1:} \quad \frac{M - \beta_0}{A} = \beta_1 + \beta_2 A + \beta_3 \frac{E}{A} + \beta_4 E.$$

From the previous parameter estimation, it was deducted that $\beta_0$ and $\beta_3$ are not significantly different from 0. Thus a first simplification arose:

$$\text{Simplified Model 1:} \quad \frac{M}{A} = \beta_1 + \beta_2 A + \beta_4 E.$$

A final conceptual simplification generated Model 2:

$$\text{Model 2:} \quad \frac{M}{A} = \beta_1 + \beta_2 \left( A + \frac{\beta_4}{\beta_2} E \right).$$

Because this is a derivation of Model 1, there was no need for further parameter estimation. The values from Table 1 were therefore substituted in the model, and the following estimated model was obtained:

$$\text{Model 2:} \quad \frac{M}{A} = 0.786 - 0.00577(A - 0.515E).$$

For further convenience, both sides of the equation was multiplied by 1,000:

$$\text{Model 2:} \quad \frac{M}{A} \times 1000 = 786 - 5.77(A - 0.515E).$$

It was proposed to name the left-hand side of the equation the 'cognitive quotient' (QuoCo).

$$QuoCo = \frac{M}{A} \times 1000.$$

In essence, this constitutes the estimated QuoCo Model: QuoCo=786−5.77(A−0.515E). If the right-hand side of the equation is defined as Standardized Age ($S_A$), where $S_A$=A−0.515E, then the estimated QuoCo Model is further simplified as:

QuoCo Model: $QuoCo=786-5.77 S_A.$

For ease of use, and with very minimal loss of precision, it is proposed that clinicians use $S_A$=A−0.5E. Since standardized age's scale uses age and education, this scale can be termed 'standardized years'. The estimated cognitive quotient model can then be formulated as QuoCo=786−5.77×$S_A$.

Figure 2A:
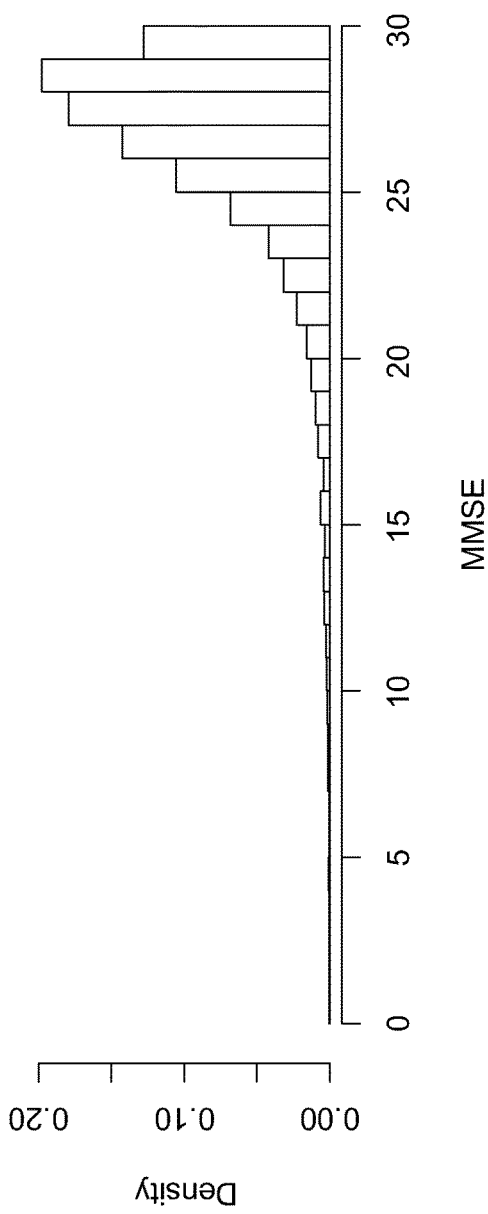
FIG. 2 presents Histograms representing the distributions of the MMSE test and cognitive quotient (QuoCo).
Figure 2B:
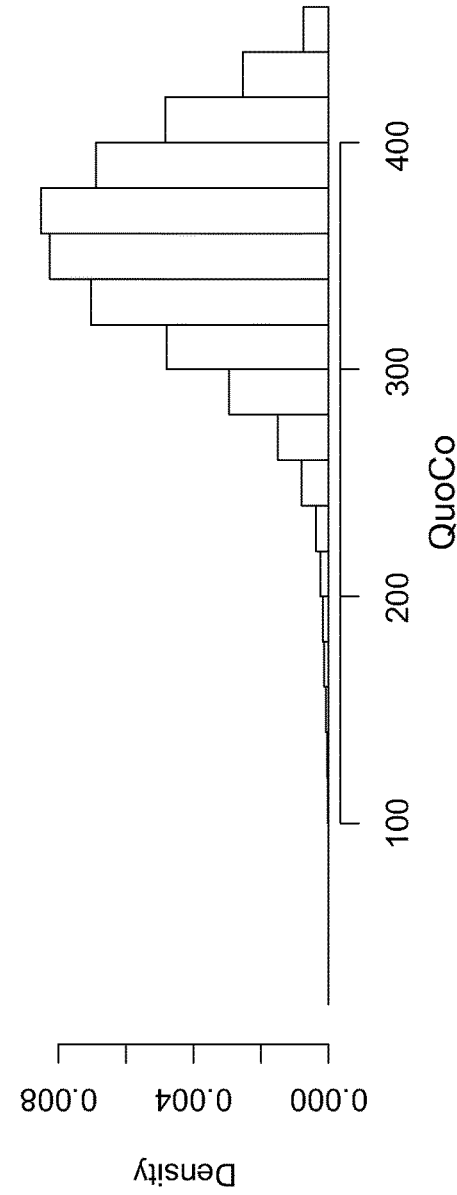

FIG. 2 illustrates the distribution of the QuoCo vs that of the non-model fitted MMSE scores.

An Underlying Theoretical Model

Though the estimated QuoCo Model is rather simple and gives the optimal parameter values, the confidence interval obtained allows one to suggest a theoretical model that can be useful for visualizing the links between QuoCo, age and education. It was postulated that the true underlying model was as follows:

$QuoCo=790-6(A-0.5E).$

Example 4—QuoCo and $S_A$ as Useful Indicators of Normal Cognitive Decline

Focus was subsequently put on the value of the proposed model in assessing whether cognitive decline followed the normal age-associated decrement path. This was conceptualized within the general goal of generating CC that allowed tracking of the QuoCo scores as a function of $S_A$. As shown above, our model suggests that QuoCo is a linear function of $S_A$. The present novel cognitive chart (CC) was therefore built using the full CSHA dataset of individuals who remained normal and individuals who developed dementia. This allowed to generate a chart that would be useful in discriminating the two groups. The obtained model plots the mean behavior of a 'normal' population. For every individual, the model was used to project QuoCo scores at 60 years of $S_A$ assuming 'normal' progression. Quantiles of this projected $QuoCo_{50}$ value were then chosen to maximize classification efficiency of the algorithm (see Proposed Classification Algorithm section below). To provide a starting point in selecting the appropriate quantiles, the average decline of the QuoCo over the average follow-up in standardized years was calculated as a predictor of a dementia diagnosis. It was found that an annual decline of 8.59 points over 7.78 standardized years is a strong predictor of dementia (it presented a sensitivity of 0.74 and specificity of 0.81, which corresponds to the maximum Youden index of 0.55). Cognitive decline charts were then built starting at the $5^{th}$ percentile, by selecting the next percentiles using a −8 rule (i.e. the slope of decline from that curve to the $5^{th}$ percentile), cognizant of the fact that such selection maximized sensitivity in that region. FIG. 3 presents the CC on which any participant's QuoCo may be plotted against their $S_A$. On this figure, each solid parallel line represents a percentile ranging from the $10^{th}$ to the $99^{th}$ percentile.

A Variable Cut-Off Zone

Illustrating the CC in a linear fashion (QuoCo as a function of $S_A$) naturally introduces a variable cut-off score. Moreover, it is well known from the literature that the MMSE varies according to age and education and cut-off scores need to be adjusted accordingly (see Folstein et al 2001, for a detailed review). Hence, a grey zone (see bottom of FIG. 3) that maximised both sensitivity and specificity was derived. Therefore, at 65 years old, the cut-off corresponds to a MMSE between 23 and 26 depending on education level while at 90 years old it corresponds to a score between 19 and 23. As well, the lowest quantiles of $QuoCo_{60}$ scores correspond to very low MMSE scores that would be considered suspect, even at a first measure.

Proposed Classification Algorithm

Based on the findings presented above, the Applicant proposes that if the initial CC measure is within the cut-off zone, then the patient should be immediately classified as having potential cognitive problems. If the patient is outside the cut-off zone, and on subsequent visits shows a decline greater than the allotted width of a percentile zone from the initial measure, e.g. started above the $85^{th}$ percentile line and cross the $65^{th}$ percentile line, then the patient should also be classified as having potential cognitive problems. Conversely, if the initial CC measure is not within the cut-off zone and on subsequent visits does not show a decline greater than the allotted width of a percentile zone from the initial measure, the patient should be classified as likely not to have cognitive problems.

Example 5—Results

Results of the proposed classification algorithm in the training CSHA sample are shown in Table 4. Sensitivity, specificity, and predictive values are given for each observed time points. Combined values obtained by modeling the relationship between diagnoses and the classifier using repeated measures logistic regression analyses are also shown. This takes into account the correlation between observations from a single individual, but estimated sensitivities, specificities and predictive values are the same as if each individual observation had been taken independently. Consequently, no confidence intervals are presented for these combined values.

TABLE 4

Sensitivity, specificity, and predictive values of the Cognitive Charts in the training CSHA sample at 95% confidence intervals.

|  | Initial measure (n = 7,569) | 5 years follow-up (n = 4,401) | 10 years follow-up (n = 2,528) | Combined |
| --- | --- | --- | --- | --- |
| Sensitivity | 80 (75-84) | 84 (79-88) | 76 (70-81) | 80 |
| Specificity | 89 (88-90) | 81 (80-82) | 88 (86-89) | 87 |
| Positive Predictive Value | 26 (24-29) | 22 (20-25) | 43 (38-47) | 29 |
| Negative Predictive Value | 99 (99-99) | 99 (98-99) | 97 (96-98) | 99 |

Abbreviations: CSHA: Canadian Study of Health and Aging[19].

For external validation purposes, the model was applied on a separate database using the NACC's UDS sample. First, a repeated measures regression was conducted to verify if the postulated relationship between the QuoCo and $S_A$ was replicated in an independent dataset. The estimated equation on the validation dataset was:

$$QuoCo = 767 - 5.51 S_A$$

and therefore remarkably close to the equation obtained in the training CSHA (CSHA Neurology 1994) dataset QuoCo Model: $QuoCo = 786 - 5.77 S_A$, mild differences being likely attributable to randomness rather than to a systematic bias. Table 5 presents the sensitivity, specificity and predictive values for the proposed algorithm using CC. Contrary to the CSHA (CSHA Neurology 1994), only healthy individuals at the initial measure were included in the NACC's UDS. Because of this, we can only estimate the specificity for the initial measure. Another difference is that patients in the NACC's UDS were evaluated every year for a maximum of ten years. Because of this, the results at 5 years and 9 years exclude patients who developed dementia prior to those dates. Additionally, results at 10 years are not presented to mirror CSHA results, given that attrition was too high by that time. Combined results that take into account the full follow-up using the same procedure as presented in Table 4 are presented and these are readily comparable between the two datasets.

TABLE 5

Sensitivity, specificity, and predictive values of the Cognitive Charts in the validation sample (NACC's UDS) at 95% confidence intervals.

|  | Initial measure (n = 7,846) | 5 years follow-up (n = 2,230) | 9 years follow-up (n = 510) | Combined |
|---|---|---|---|---|
| Sensitivity | — | 65 (53-76) | 57 (29-82) | 64 |
| Specificity | 98 (98-98) | 92 (91-93) | 92 (90-95) | 93 |
| Positive Predictive Value | — | 17 (13-22) | 19 (8-33) | 10 |
| Negative Predictive Value | — | 99 (99-99) | 99 (97-99) | 99 |

Abbreviations: NACC's UDS: National Alzheimer's Coordinating Center's Uniform Data Set[21]

Figure 4:
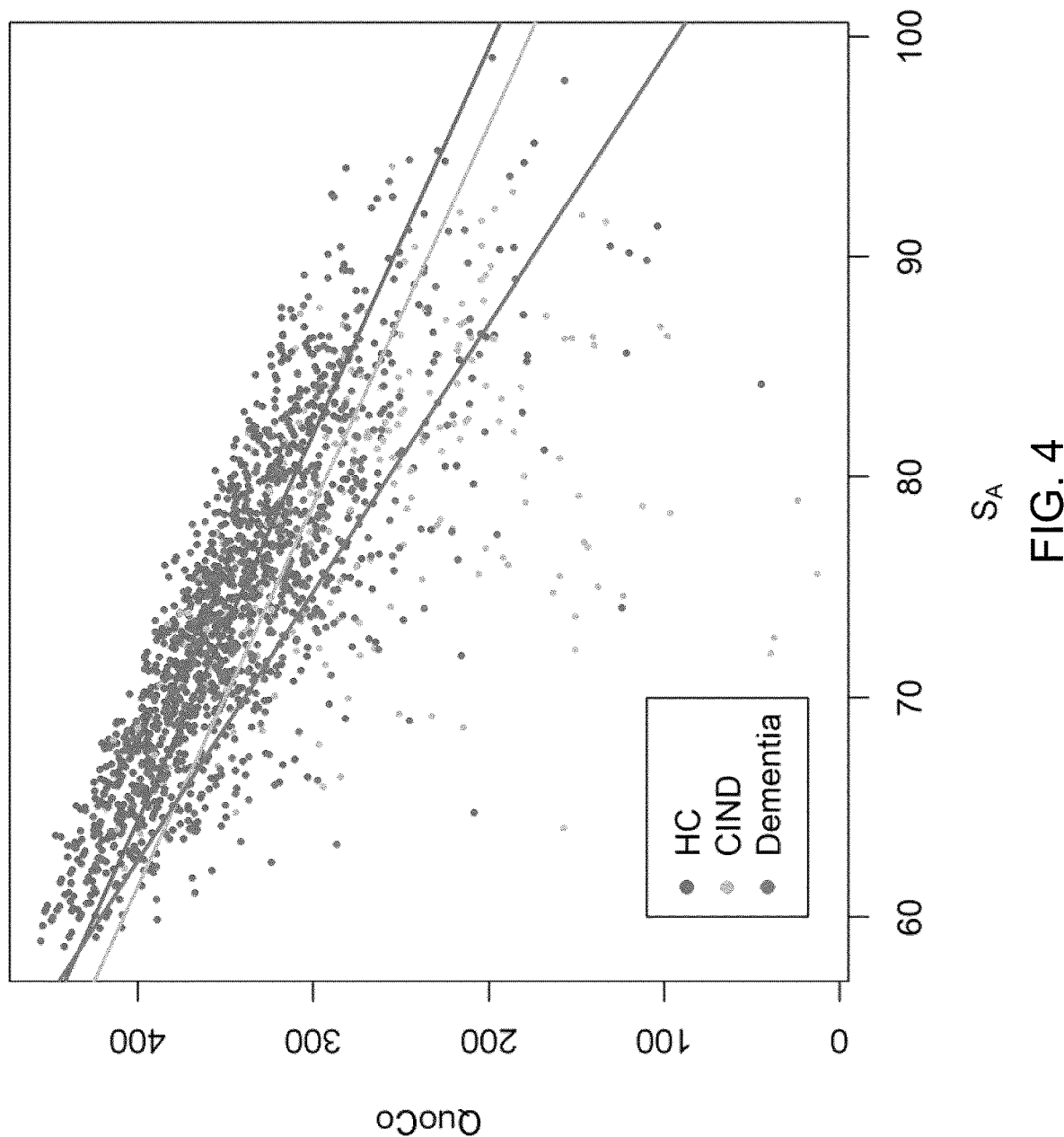
FIG. 4 is a graphical representation of the relationship between standardized age ($S_A$) and the cognitive quotient (QuoCo) for Healthy Controls (HC), Cognitive Impairment No Dementia (CIND), and Dementia.

Cognizant of the fact that CIND are not equivalent to MCI, the general trend of HC, CIND, and the Dementia group using a mixed effect repeated model (see FIG. 4) were nonetheless explored. There was a significant group effect (p<0.0001) whereby the Dementia group differed from HC at baseline. Furthermore, the Dementia group declined more significantly than HC over time (p<0.0001) but there were no differences between HC and CIND over time.

Example 6—Discussion

This section introduces the methods used to develop the CC. The model was based on a training sample of 6,411 healthy control individuals aged 65 years or older from the CSHA who completed MMSE at baseline, 5 and 10 years. As suggested by cubic smoothing splines, it was postulated that age was quadratically associated with MMSE while a linear relationship appeared between education and MMSE; the latter becoming null past 14 years of education. The QuoCo and $S_A$ were modelled into a final equation using repeated measures regression representing key indicators of age-associated cognitive decline. It was proposed that if on initial measure the patient's position on the CC was outside the cut-off zone, or on subsequent clinical visits showed a decline greater than the allotted width of a percentile zone from the initial measure, then the patient should be classified as having possible cognitive problems. Results of the repeated measures logistic regression analyses conducted on the CSHA sample of both the 6,411 HC and 1,158 dementia cases using the proposed classification algorithm, yielded high sensitivity, specificity and predictive values. Furthermore, they were comparable to an external validation sample of n=7,846 based on NACC's UDS. As a rule, a decline greater than one percentile zone from initial measure suggested a significant cognitive decline and distinguished HC from those who developed dementia with a sensitivity of 80%, a specificity of 89% and a very high negative predictive value of 99%. Model fitting of the data was conducted using standard statistical procedures and data was derived according to common mathematical principles. The proposed classification rule was also based on pathological data within the training sample and is a common concept used in Pediatrics to signal any distancing from normal values. Finally, both sets of analyses, either on the training or the validation sample, yielded similar patterns of findings, hence supporting the model.

Calculations performed on the validation sample obtained through NACC's UDS open access data process was remarkably comparable to the training sample in terms of its size, power, recruitment modalities, standardized evaluation format, consensus diagnoses, longitudinal design (annual follow-up) and informed consent. There were some differences however between the two samples. Participants in NACC's UDS were slightly younger, more educated and cognitively healthier at study start that the training sample. Furthermore, incidence of delirium appeared lower in NACC's UDS. Nonetheless, this did not have a significant impact as the equation modeled on NACC was similar to that on CSHA.

Model fitting of the CC is not without limitations. The equation proposed herein is as reliable as the underlying components used to build it. The CSHA itself was not without flaws. It was initiated more than two decades ago and one could wonder if this precious set of data still applies to elderly populations today. The underlying and essential building block of the CC remains the MMSE. This cognitive test has been criticized over the years. Yet, it remains the most widely used cognitive screening measure worldwide. Even in tertiary memory clinics composed of dementia experts, the MMSE is administered as an ice-breaker to identify an individual's general cognitive performance. The power of this tool relies in its ability to be used simply and efficiently over repeated measures, such as in CSHA. And as long as the MMSE is interpreted within its limitations, it will remain a very useful screening test.

Example 7—Application of Cognitive Charts

Introduction—Cognitive Charts Generated in Examples 1-4—Model Fitting can be Conceptualized as Cognitive Decline Curves Associated with Normal Aging Similar to 'growth curves' used in Pediatrics for a child's growth, a patient can be followed-up by first-line physicians over many years with single MMSE observations as he/she ages. Beyond simple normative data, CC provides a ready-to-use chart which accounts for age and education, two key predictors of incipient decline on MMSE. While abrupt distancing from expected aging trajectory can happen as a result of an infection or trauma for instance, progressive and insidious deterioration may indicate the early signs of a degenerative process. Altogether, CC can help health professionals make sound evaluations of their elderly patients' cognitive functioning and evolution over time. Example 7—Application of Cognitive Charts, illustrates the practical use of CC based on real patients followed over the years using the MMSE. The role of the cut-off zone is further illustrated.

Methods and Results

FIG. 3 shows the CC in accordance with an embodiment. Each solid parallel line represents a chosen percentile to illustrate the data. The dotted lines are placed at the exact midline between plain lines for easier follow-up of decline. The QuoCo decline in HC is almost constant over time. As a rule, if the initial measure on the CC is within the cut-off zone (illustrated in grey), then the patient can be immediately classified as having potential cognitive problems. By contrast, if the patient is outside the cut-off zone, and on subsequent visits shows a decline greater than the allotted width of a percentile zone from the initial measure, e.g. started on (or above) the 85th percentile line and crossed the 65$^{th}$ percentile line, then the patient can be classified as having potential cognitive problems.

Three Representative Cases

Figure 5A:
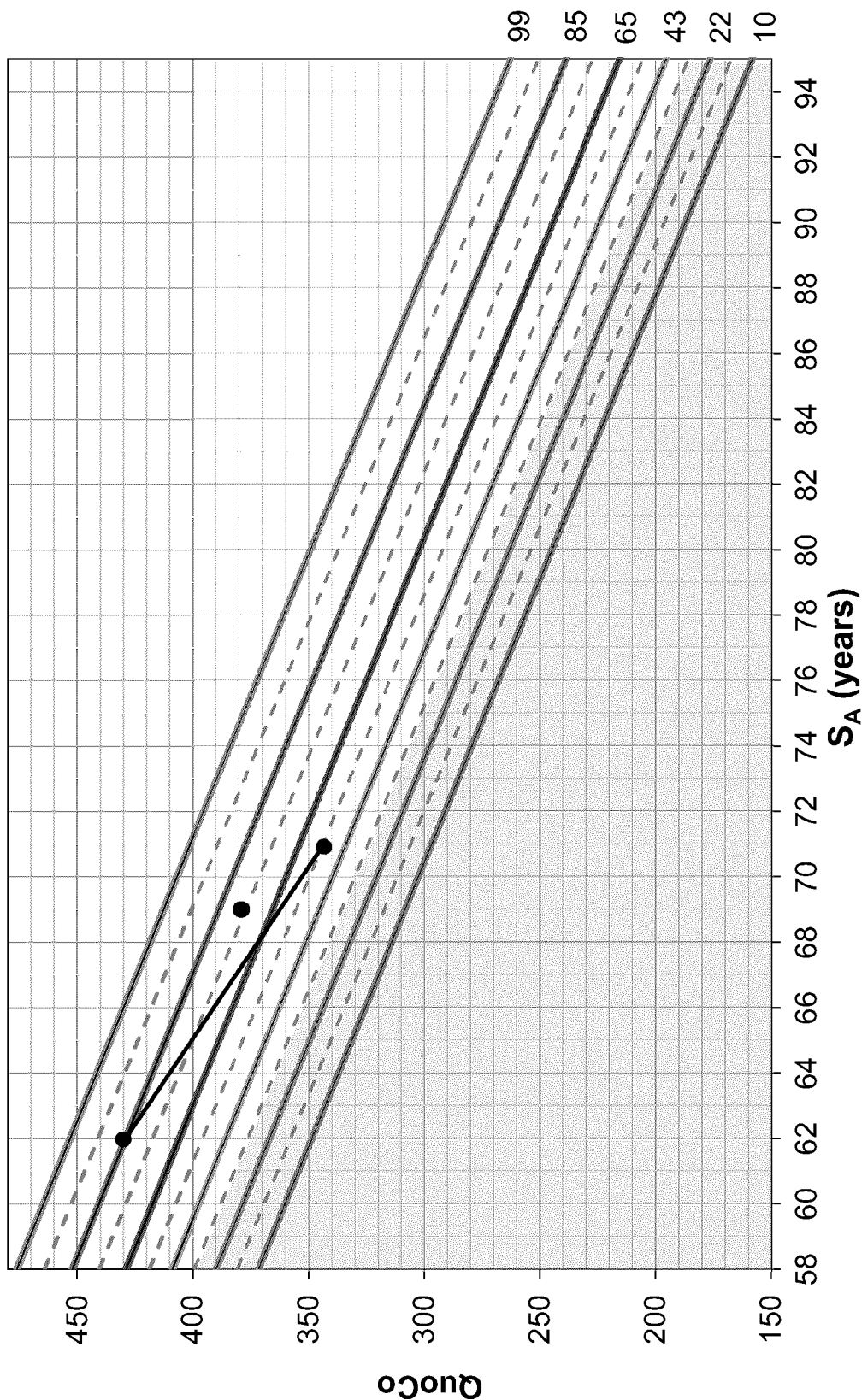
FIGS. 5A to 5C show Cognitive Charts for different representative clinical cases.
Figure 5B:
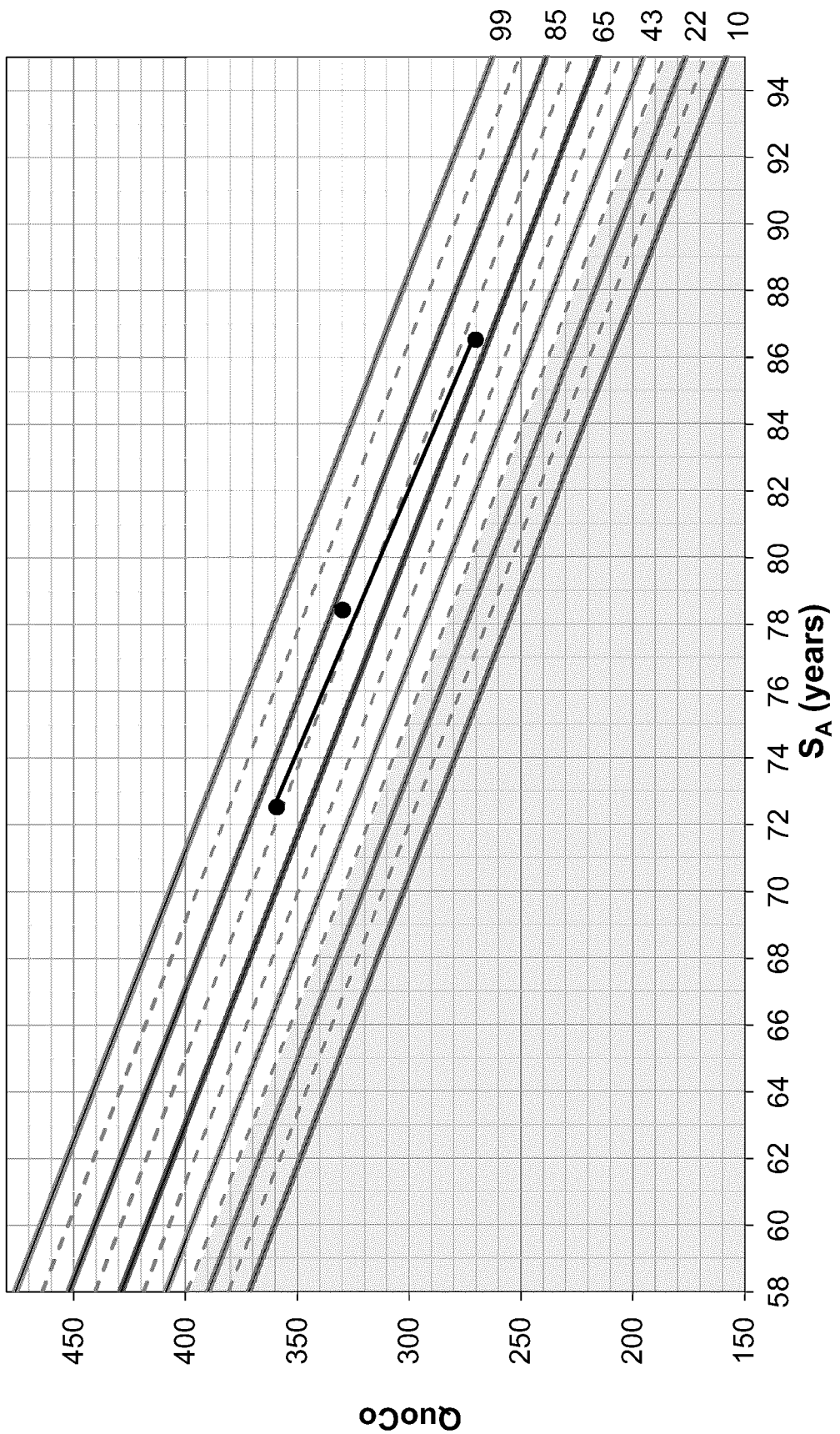
Figure 5C:
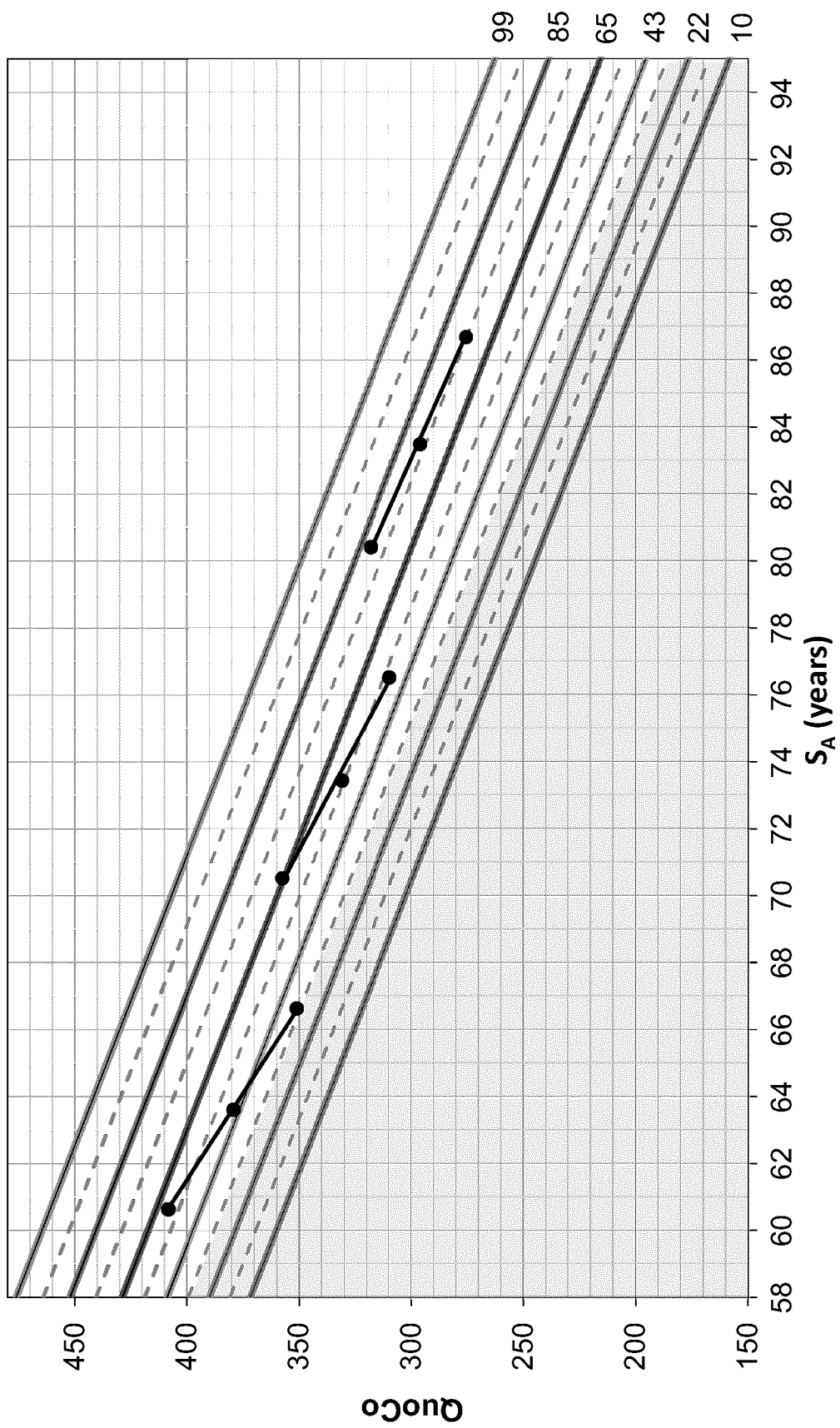

FIG. 5A to 5C present three representative cases for which the CC can be helpful in daily practice.

Case A (FIG. 5A). A 76-year-old female is brought to her physician by her son because of memory problems. She has a Grade 10 education. Previously, a baseline MMSE (29/30) was completed at age 67. The physician calculated her QuoCo=29/67×1,000=433 (QuoCo=MMSE/age×1,000), and her $S_A$=67−0.5×10=62 ($S_A$=age−0.5×years of education). These results were used to plot her performance on the CC (see FIG. 5A). Later at 74 years old she had another MMSE (28/30) and calculations of her QuoCo (378) and $S_A$ (69) were also charted on her CC. The overall profile of decline is acceptable since she remains within one percentile interval zone. She presented recently at 76 years of age and again, her MMSE was completed indicating a performance of 26/30 (QuoCo=342, $S_A$=71), that is only 2 points below her previous performance. As shown on her CC, however, this last performance represents a total decline greater than 1.5 percentile interval zone from baseline (we recommend that the clinician interprets the general longitudinal decline by tracing a line from baseline to most recent data), and therefore is probably abnormal. Her physician also queries about functional abilities. Her son indeed reported mild decline in her ability to manage her finances and to cook. Further investigation was recommended. The patient was eventually referred to a memory clinic where mild AD was diagnosed.

Case B (FIG. 5B). This 89-year-old man was admitted to Geriatrics for repeated falls. During hospitalization, questions came up about his cognitive skills. His MMSE was 24/30. This result appeared low but his family explained that he had only completed 5 years of schooling. Looking into the patient's past medical charts, two previous MMSE performance were found both indicating 27/30 (one at 75 years old and the other at 81 years old). All of these were charted on the CC (75 years old: QuoCo=360, $S_A$=72.5; 81 years old: QuoCo=333, $S_A$=78.5; 89 years old: QuoCo=270, $S_A$=86.5) (see FIG. 5B). Surprisingly, his profile remained within one percentile interval zone which was considered longitudinally normal. During recovery, his preserved cognitive skills emerged and he was scheduled for a six-month follow-up visit.

Case C (FIG. 5C). Three patients were followed up on CC on three visits, at three year intervals, over a period of 6 years (see FIG. 5C). The first case (left) is a 68 year-old female, the second (middle) is a 78 year-old male, and the last (right) is an 88 year-old male. Each completed 15 years of education and showed similar results on the MMSE on each of the three visits (28/30; 27/30; 26/30). Which patient is not following his expected cognitive decline? Answer: the patient on the left because she is crossing one percentile interval zone.

Six Additional Illustrative Cases

Figure 6A:
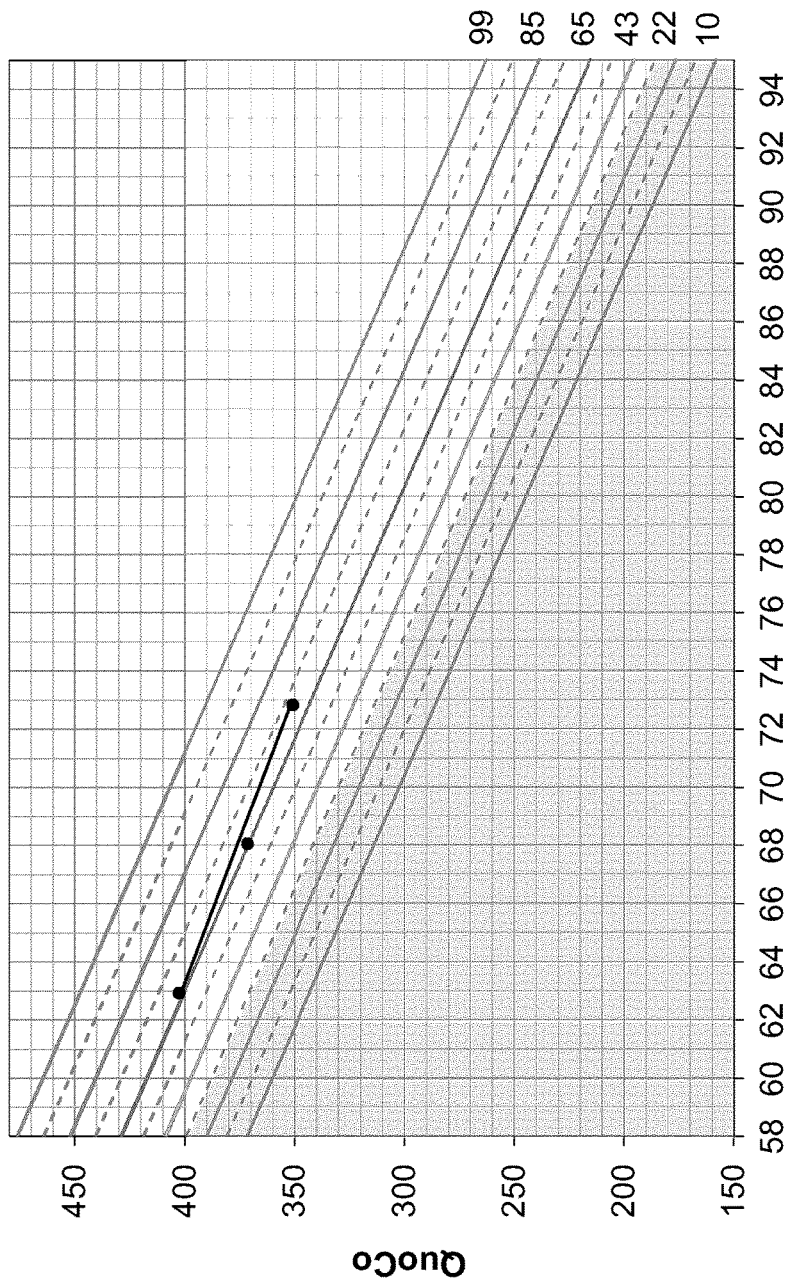
FIGS. 6A to 6F show Cognitive Charts for six additional illustrative cases.
Figure 6B:
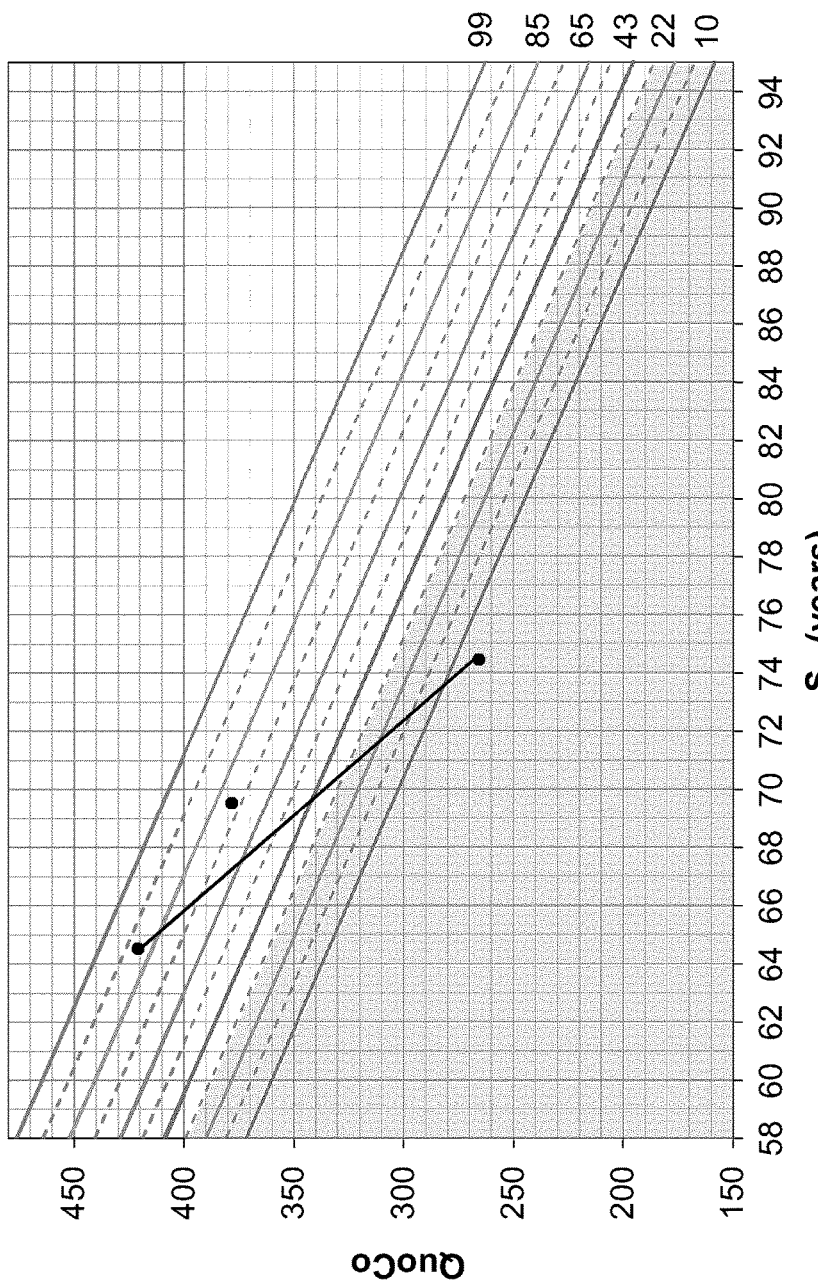
Figure 6C:
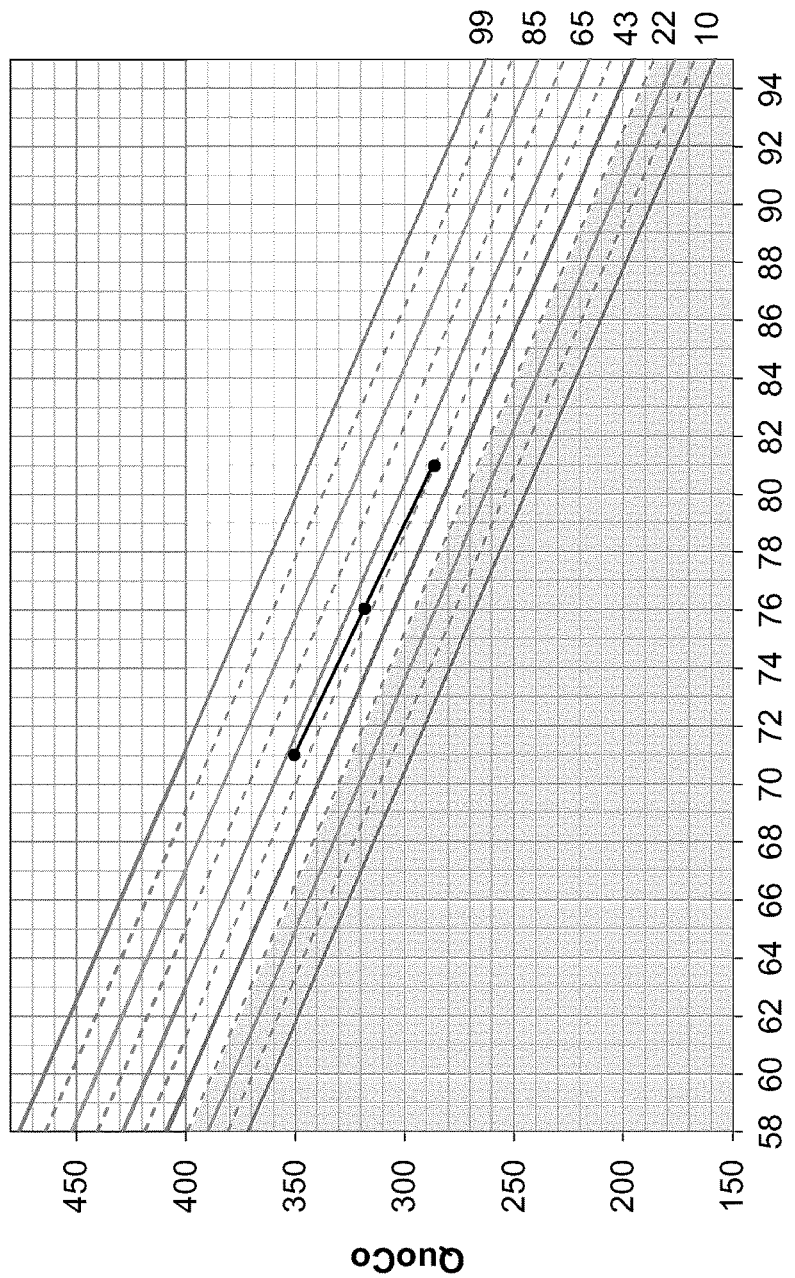
Figure 6D:
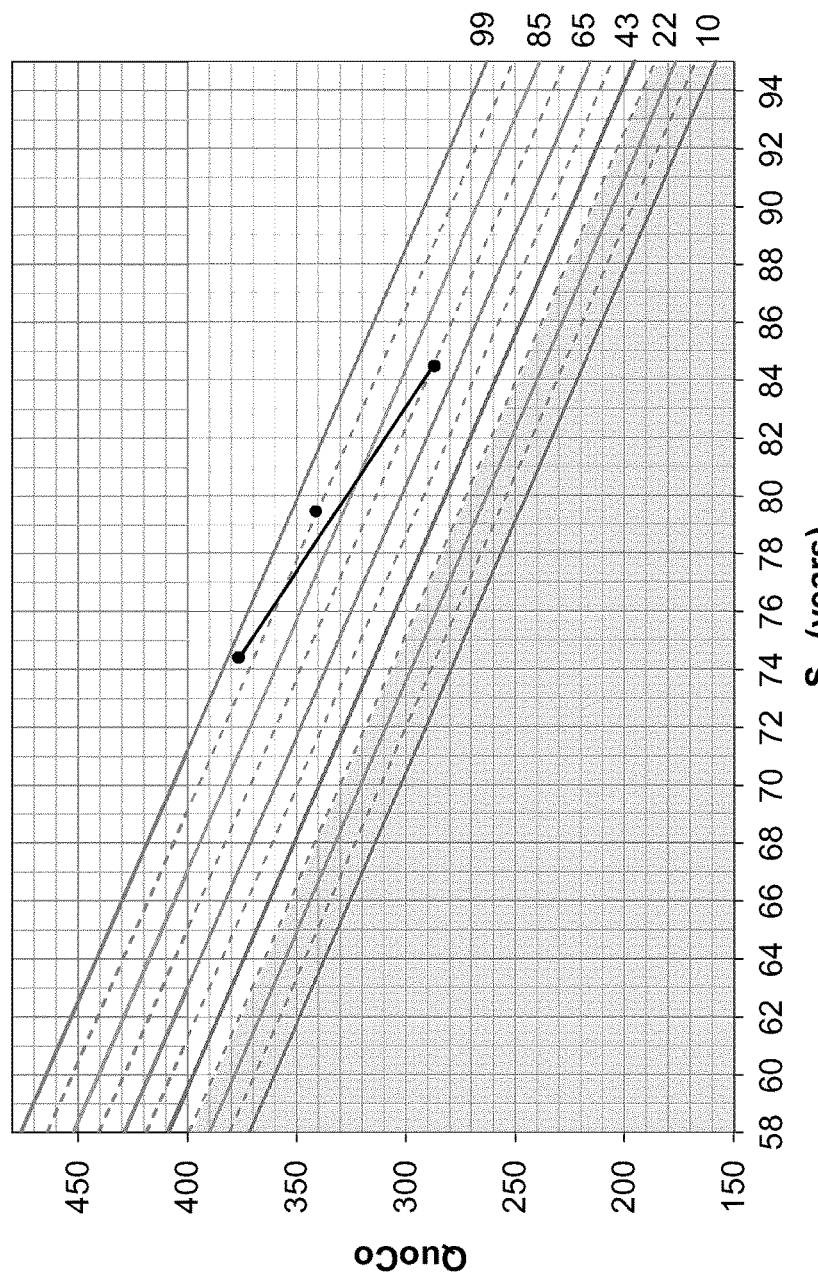
Figure 6E:
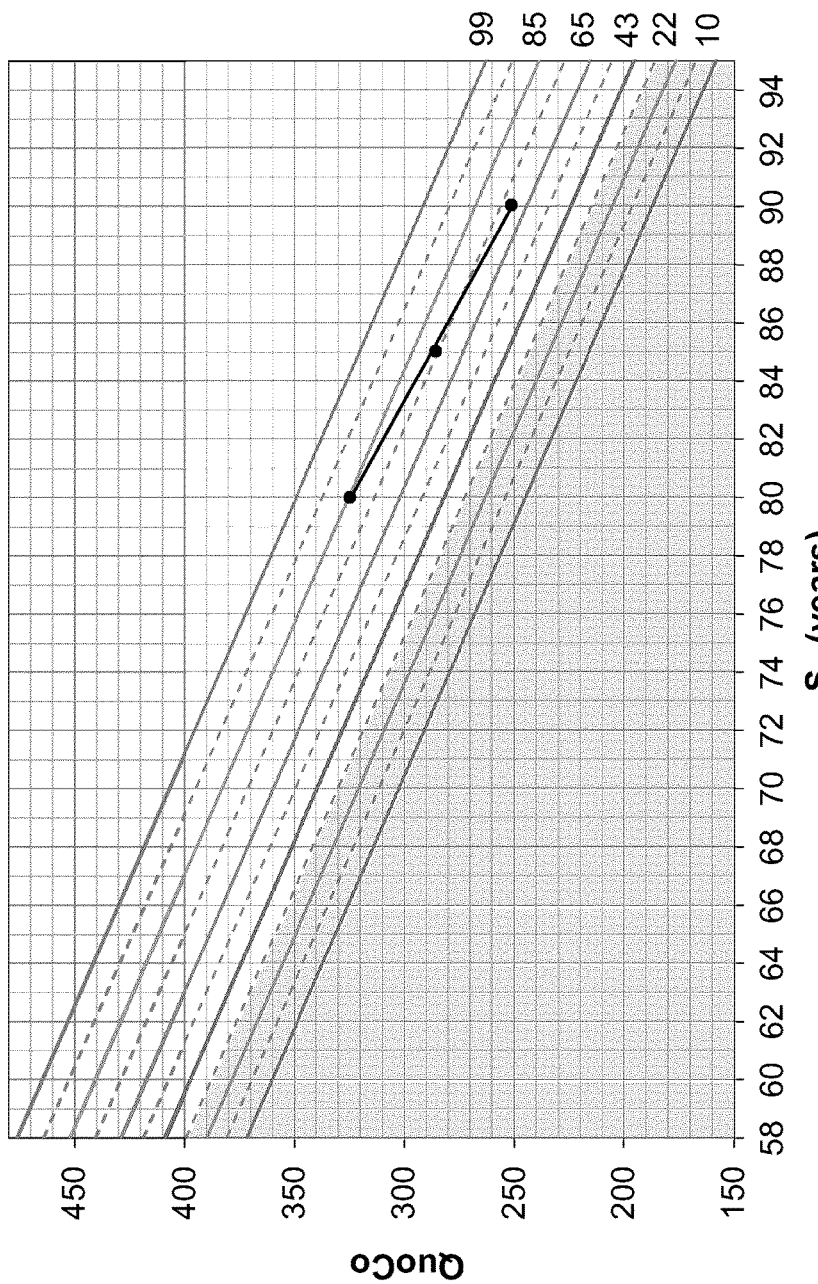
Figure 6F:
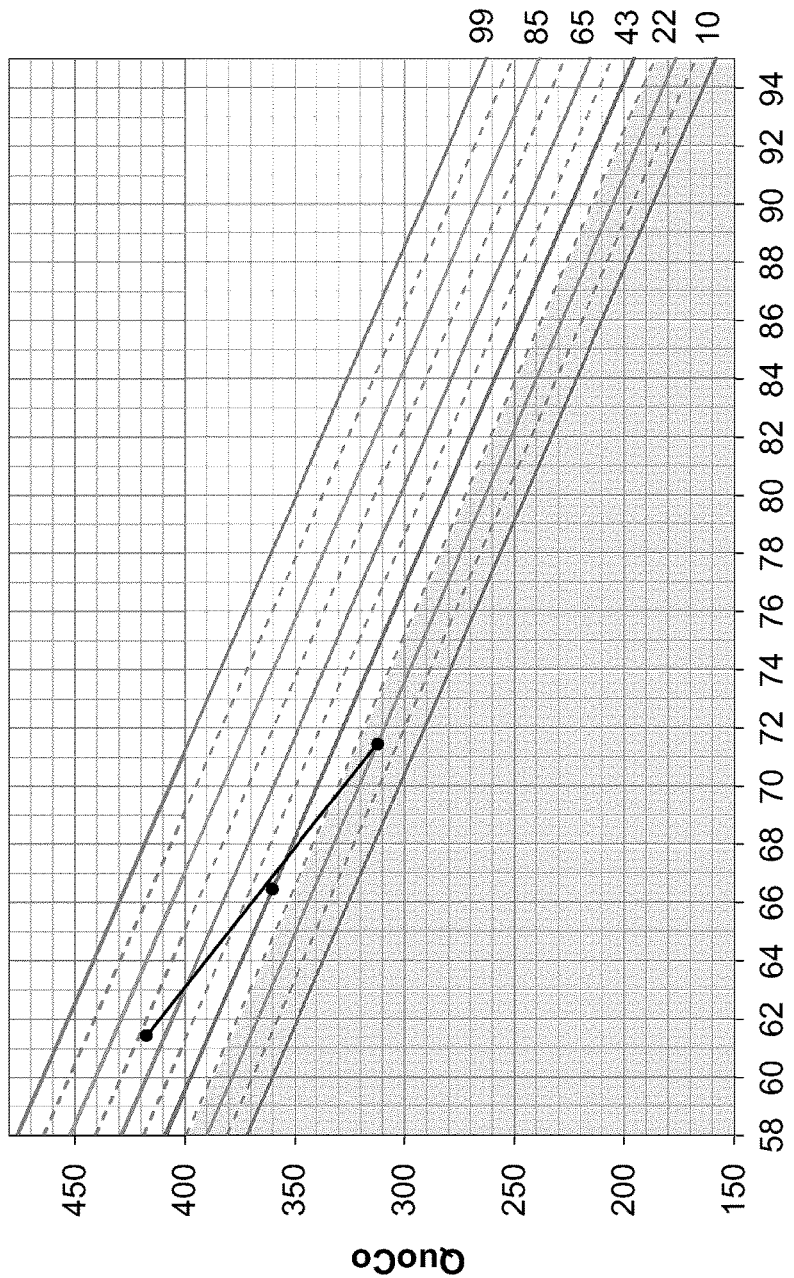

Additional illustrative cases are shown in FIGS. 6A to 6F. The case shown in FIG. 6A has 25 years of education and similar performance on MMSE (28/30) throughout the years. Here, age does not have an impact on the longitudinal CC trajectory which remains along the 65$^{th}$ percentile line. The case shown in FIG. 6B has 9 years of education. As age increases from 69 to 74 years old, with similar MMSE scores (29 and 28, respectively), trajectory is relatively unchanged even though education is much lower when compared to the case shown in FIG. 6A. When the MMSE drops from 28 at age 74 to 21 at age 79, CC reveals the anomaly. Of course, a drop of 7 points on the MMSE would have alerted any clinician but the CC further illustrates the severity of the phenomenon. The case shown in FIGS. 6C and 6D show the classic situation where a cut-off of 26 on the MMSE is inappropriate. Indeed, both cases show a normal longitudinal trajectory despite hitting the proposed MMSE cut-off of 26/30. The case shown in FIGS. 6E and 6F present similar MMSE scores of 28-26-24, but for patients in different age groups. Results indicate a normal trend for the 86-year-old patient but not the 67 year-old. These cases provide additional examples of the strengths of the method.

Discussion

Recent epidemiological work from various international groups converges towards one conclusion, namely that dementing illnesses have reached pandemic levels. In many respects, early detection of cognitive impairment remains our best approach to early disease management before irreversible brain damage is done. Family physicians are in a key position to contribute to this endeavor, but in daily practice this goal remains difficult to attain. This is partly due to the fact that patients' cognitive trajectories are poorly charted longitudinally. Hence it was sought to generate simple and ready-to-use CC for clinical follow-up of age-related cognitive decline based 1) on the most widely used screening measure worldwide, the MMSE (even though in different embodiments other screening tests could be used), and 2) the widely known concept of growth charts used in medicine. A large Canadian cohort (n=7,569, including 6,411 HC and 1,158 dementia cases) of cognitively normal community dwelling individuals were followed up over 10 years between 1991 and 2001 with cognitive assessments at three specific points in time. Mathematical model fitting was used to predict normal cognitive decline in relation to age, education and MMSE scores and to distinguish normal from abnormal cognitive decline. Similar to 'growth charts', the CC allow physicians to position any patient based on age, education and MMSE scores, and simply track its longitudinal profile of cognitive decline over time. The implications are critical as this could prompt earlier intervention for an older adult who 'fell off' the curve. More precisely, a decline on the CC should prompt further detailed investigation according to the Canadian Consensus Conference on the Diagnosis and Treatment of Dementia (or CCCDTD4) while absence of decline reliably identifies those individuals who do not need further cognitive work up and follow age-associated cognitive decline.

Age-Associated Cognitive Decline

Cognitive decline associated with aging is a universal finding. In some efforts, MMSE scores have declined to as far as 15/30 points for the lowest quartile of the oldest olds in cognitively normal older adults. On the other hand, persons with higher educational attainment often show higher MMSE scores, thus complicating discrimination between normal cognitive decline with aging and MCI. Other authors have measured the longitudinal evolution of MMSE distribution in a sample of patient's age 75 years and older and again found age to be associated with MMSE scores. The present findings are consistent with previous work showing that higher levels of education are associated with better cognitive performance but not more rapid rate of decline. The present evaluated rates of decline in HC are in the same range as previous large studies using the MMSE. By contrast, the present data shows that these rates are not constant and tailored by $S_A$ as well as by original baseline performance. This may explain why previous reports support a high MMSE decline (approximately 5 points) to attain significance on a whole group of patients. Similar to previous efforts, our data also showed that MMSE scores were not affected by gender.

Normal vs. Abnormal Cognitive Decline, Cut-Off Scores and the Use of Normative Data Distinguishing normal from abnormal cognitive decline over time is no simple task in the elderly patient. Clinicians often use a fixed cut-off of 23/30 on the MMSE but others have suggested that modulated cut-offs (between 23 and 26) are more accurate. Our data show that a fixed cut-off may not accurately represent the longitudinal trajectory of an individual's performance (see for example FIGS. 6C and 6D). Age and education have an important impact on the range of normal scores. MMSE scores are affected by age and education level, with lower scores being associated with increasing age and lower educational level. Normative data adjusting for age and/or education already exist and are useful to appreciate individual MMSE scores. However, cross-sectional norms are often limited by cohort effects. Moreover, they generally do not provide a general picture of the longitudinal profile of cognitive decline. Longitudinal observation of MMSE scores over time is rare and usually based on short follow-up studies.

Most importantly, physicians often do not use them; physicians find it difficult to chart a patient over time using percentile tables. By contrast, the CC presented in this paper combines age and education within the same graph, and gives an opportunity to apply the well-known medical concept of growth charts using longitudinal data to disentangle normal vs. abnormal cognitive aging. This Cognitive Chart (CC) extrapolates beyond simple percentiles and provides continuous curves of normal expected decline with aging. In this model, such changes become invariant from age and education and are based on the largest Canadian cohort of normal elderly individuals. This is a major advantage when compared to percentile tables which categorize individuals into specific pre-determined boxes while ample data suggest that intervals in normative tables are not constant (being driven differently by age and education at different spectra of the continuum being measured).

The classification algorithm developed based on the CC yields high sensitivity, high specificity and very high negative predictive value. The classification algorithm proved equal to a cut-off approach while offering numerous critical advantages over and beyond cut-off scores: 1) longitudinal tracking of performance 2) better assessment of high initial Mini-Mental State Examination scores, 3) less vulnerability to ceiling and floor effects, 4) visually combining age and education on the same graph, 5) less statistical variations in sensitivity and specificity over time and population subgroups (age, gender, education), and 6) a visual representation of the concept of cognitive reserve. Finally, external validation on a separate dataset (National Alzheimer's Coordinating Center's Uniform Data Set[25]), a key validity test of a model-based approach, proved the cognitive charts to be highly valid, reliable and an improvement over the use of a simple MMSE cut-off.

CONCLUSION

Using the largest sample of longitudinal data on healthy Canadians, a model of normal age-associated decline using MMSE was developed. As mentioned above, in alternative embodiments, other tests could be used. The QuoCo accounts for variable impact of age, $S_A$ factors in education, and formulated together in the CC they bring all participants on a similar scale. To our knowledge, this is the first time that MMSE, age and education have been combined in CC to allow early detection and prospective follow-up of age-associated cognitive decline in a straight-forward and clinically accessible fashion. Similar to 'growth charts' used worldwide in medicine, CC represents an innovative method to determine whether elderly patients show normal vs. abnormal performance on serial MMSE. A significant decline on CC should prompt further detailed investigation in line with CCCDTD4 recommendations while a non-significant decline reliably identifies those individuals who do not need further cognitive work up.

Several alternative embodiments and examples have been described and illustrated herein. The embodiments of the invention described above are intended to be exemplary only. A person skilled in the art would appreciate the features of the individual embodiments, and the possible combinations and variations of the components. A person skilled in the art would further appreciate that any of the embodiments could be provided in any combination with the other embodiments disclosed herein. It is understood that the invention may be embodied in other specific forms without departing from the central characteristics thereof. The present examples and embodiments, therefore, are to be considered in all respects as illustrative and not restrictive, and the invention is not to be limited to the details given herein. Accordingly, while specific embodiments have been illustrated and described, numerous modifications come to mind without significantly departing from the scope of the invention as defined in the appended claims.

The invention claimed is:

1. A method for generating a tool for detecting and/or classifying cognitive decline in a patient, the method comprising:
    a) identifying at least one patient parameter variable over time in a sample of data including cognition test scores substantially influenced by the at least one patient parameter;
    b) performing a regression analysis from the sample of data and generating an original regression model therefrom;
    c) estimating parameters of the original regression model using one of a Maximum Likelihood Method and a Least Mean Squares method;
    d) generating a simplified regression model from the original regression model and the estimated parameters; and
    e) generating a cognitive chart based on the simplified regression model and built using the sample of data, the cognitive chart allowing a mapping of a score at least partially based on a patient cognition test score, as a function of a second parameter at least partially based on one of the at least one patient parameter, the cognitive chart comprising a plurality of spaced apart percentile lines each representing a chosen percentile, with the area between two adjacent lines of the plurality of percentile lines defining a percentile zone which allow detection of abnormal cognitive decline over time, and a cut-off zone indicative of potential cognitive decline problems for the patient;

f) performing at least one of detecting and classifying the cognitive decline in the patient by mapping of the score at least partially based on the patient cognition test score, as a function of the second parameter at least partially based on the one of the at least one patient parameter.

2. The method of claim 1, wherein the at least one patient parameter comprises an age of the patient and a number of years of schooling of the patient and wherein the original regression model comprises at least one of the at least one patient parameter as a quadratic factor.

3. The method of claim 2, wherein the original regression model comprises the age of the patient as a quadratic factor, the number of years of schooling of the patient as a linear factor and an interaction between the age of the patient and the number of years of schooling of the patient, the original regression model being defined as:

$$M=\beta_0+\beta_1 A+\beta_2 A^2+\beta_3 E+\beta_4 A\cdot E$$

wherein M corresponds to the patient cognition test score, A corresponds to the age of the patient, E corresponds to the number of years of schooling of the patient and $\beta_0$, $\beta_1$, $\beta_2$, $\beta_3$, $\beta_4$, each correspond to a constant.

4. The method of claim 3, wherein the simplified regression model is defined as:

$$\frac{M}{A} = \beta_1 + \beta_2\left(A + \frac{\beta_4}{\beta_2}E\right).$$

5. The method of claim 2, wherein the step of generating the cognitive chart based on the simplified regression model further comprises defining at least one standardized parameter from the simplified regression model and using each one of the at least one standardized parameter as an axis of the cognitive chart, the at least one standardized parameter comprising:

a cognitive quotient (QuoCo) defined as:

$$QuoCo=(M/A)*C_1$$

wherein M corresponds to the patient cognition test score, A corresponds to the age of the patient and $C_1$ corresponds to a first constant; and a standardized age ($S_A$) defined as:

$$A-(C_2*E)$$

wherein A corresponds to the age of the patient, $C_2$ corresponds to a second constant and E corresponds to the number of years of schooling of the patient.

6. The method of claim 5, wherein the at least one standardized parameter is configured to define a linear simplified regression model used for generating the cognitive chart.

7. The method of claim 1, further comprising the step of displaying the cognitive chart on a digital medium or a physical medium, for subsequent use in aiding detection, diagnosis or follow-up of cognitive decline in a patient.

8. The method of claim 7, wherein the step of displaying the cognitive chart on the digital medium or the physical medium comprises printing the cognitive chart on the physical medium.

9. A computer readable memory having recorded thereon statements and instructions for execution by a computer, with the statements and instructions comprising code for performing the steps of claim 1.

10. A computer program product comprising a computer readable memory storing computer executable instructions thereon that when executed by a computer perform the steps of claim 1.

11. A method for diagnosing or classifying cognitive decline in a patient, the method comprising the steps of:
 a) determining a cognitive test score for said patient;
 b) obtaining an age of said patient;
 c) obtaining a number of years of schooling of said patient;
 d) calculating a cognitive quotient (QuoCo) as QuoCo=test score/age×$constant_1$ for said patient;
 e) calculating a patient parameter variable for said patient;
 f) plotting at least a first QuoCo measure point on a cognitive chart (CC) for the corresponding patient parameter variable, said CC being defined as a chart having:
  a first axis defining values the QuoCo;
  a second axis defining values of the patient parameter variable;
  a first area of the chart defining a cut-off zone indicative of potential cognitive problems for the patient;
  a second area positioned outside of the first area and being indicative of the patient being likely to have no cognitive problems, the first area and the second area being visually differentiable; and
  a plurality of parallel percentile lines spaced apart from one another and each representing a chosen percentile, with the area between two adjacent lines of the plurality of percentile lines defining a percentile zone which allow detection of abnormal cognitive decline over time; and
 g) determining at least one of:
  whether any single contemporaneous QuoCo measure point is positioned within the cut-off zone of said CC, whereby the patient is then classified as having potential cognitive problems; or
  whether a single contemporaneous QuoCo measure point is positioned within the second area of said CC, whereby the patient is then classified as likely to have no cognitive problem.

12. The method of claim 11, wherein the step of plotting at least a first QuoCo measure point on the cognitive chart (CC) includes plotting an additional QuoCo measure point on the cognitive chart (CC) and the method further includes drawing a line connecting the first QuoCo measure point and the additional measure point; whereby when said line shows a decline greater than an allotted width of a percentile zone from said first QuoCo measure point in said CC, the patient is then classified as having potential cognitive problems.

13. The method of claim 11, wherein the cognitive quotient is defined as QuoCo=test score/age×1000 and wherein said cognitive test includes a Mini-Mental State Examination (MMSE).

14. The method of claim 11, wherein said CC is further defined as a standardized age CC in which the second axis defines values of a standardized age ($S_A$) as the patient parameter variable and wherein the step of calculating a patient parameter variable for said patient includes calculating a standardized age ($S_A$) as: $S_A$=age−$constant_2$×# years of schooling for said patient.

15. The method of claim 14, wherein the standardized age ($S_A$) is defined as: age−0.5×# years of schooling for said patient.

16. A computer readable memory having recorded thereon statements and instructions for execution by a computer, with the statements and instructions comprising code for performing the steps of claim 11.

17. A computer program product comprising a computer readable memory storing computer executable instructions thereon that when executed by a computer perform the steps of claim 11.

\* \* \* \* \*